United States Patent
Le Maire et al.

(10) Patent No.: US 11,071,701 B2
(45) Date of Patent: *Jul. 27, 2021

(54) MEDICAMENT AND COSMETIC COMPOSITION COMPRISING RESORCINOL DERIVATIVES

(71) Applicant: Symrise AG, Holzminden (DE)

(72) Inventors: Marielle Le Maire, Boulogne, FL (US); Imke Meyer, Bodenwerder (DE); Gabriele Vielhaber, Colombes (FR); Gerhard Schmaus, Höxter (DE)

(73) Assignee: Symrise AG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/310,240

(22) PCT Filed: Jun. 30, 2016

(86) PCT No.: PCT/EP2016/065329
§ 371 (c)(1),
(2) Date: Dec. 14, 2018

(87) PCT Pub. No.: WO2018/001485
PCT Pub. Date: Jan. 4, 2018

(65) Prior Publication Data
US 2019/0183760 A1 Jun. 20, 2019

(51) Int. Cl.
*A61K 8/34* (2006.01)
*A61Q 17/04* (2006.01)
*A61Q 19/02* (2006.01)

(52) U.S. Cl.
CPC .............. *A61K 8/347* (2013.01); *A61Q 17/04* (2013.01); *A61Q 19/02* (2013.01)

(58) Field of Classification Search
CPC ......... A61K 8/347; A61Q 19/02; A61Q 17/04
See application file for complete search history.

(56) References Cited

U.S. PATENT DOCUMENTS

| 4,959,393 | A | * | 9/1990 | Torihara | ................ | A61K 8/347 |
| | | | | | | 514/724 |
| 6,132,740 | A | | 10/2000 | Hu | | |
| 2003/0185773 | A1 | | 10/2003 | Love et al. | | |
| 2008/0069784 | A1 | * | 3/2008 | Millikin | ................ | A61K 8/27 |
| | | | | | | 424/59 |
| 2009/0162305 | A1 | * | 6/2009 | Vielhaber | ................ | A61Q 5/08 |
| | | | | | | 424/62 |
| 2009/0263513 | A1 | | 10/2009 | Marini | | |
| 2010/0143267 | A1 | | 6/2010 | Pertile et al. | | |
| 2011/0152372 | A1 | | 6/2011 | Mallard et al. | | |
| 2015/0064122 | A1 | | 3/2015 | Meyer et al. | | |
| 2015/0110725 | A1 | | 4/2015 | De Paoli Ambrosi | | |
| 2016/0015614 | A1 | * | 1/2016 | Mann | ................ | A61K 8/49 |
| | | | | | | 424/59 |
| 2016/0030321 | A1 | | 2/2016 | Dreher | | |
| 2016/0067163 | A1 | | 3/2016 | Meyer et al. | | |

FOREIGN PATENT DOCUMENTS

| EP | 2853254 A1 | | 4/2015 |
| FR | 2900046 A1 | | 10/2007 |
| FR | 2958156 A1 | | 10/2011 |
| FR | 2958845 A1 | | 10/2011 |
| WO | 2014/170239 | * | 10/2014 |
| WO | 2015011311 A1 | | 1/2015 |

OTHER PUBLICATIONS

Definition of "non-therapeutical" by Merriam-Webster; downloaded from https://www.merriam-webster.com/dictionary/nontherapeutic on Oct. 2, 2019. (Year: 2019).*
Jones, title: Visible Light Spectrum Overview and Chart; publishe Feb. 2, 2019. downloaded from https://www.thoughtco.com/the-visible-light-spectrum-2699036?print on Oct. 2, 2019 (Year: 2019).*
Beth Sissons, title:What to know about hyperpigmentation; Last reviewed by Cobb on Mon Nov. 26, 2018. Downloaded from https://www.medicalnewstoday.com/articles/323808.php) on Oct. 2, 2019. (Year: 2018).*
Taieb et al.; Title: Diagnosis of some common and uncommon hyperpigmentation disorders in children; Dermatologica Sinica; vol. 32, Issue 4, Dec. 2014, pp. 211-216. (Year: 2014).*
Unknown author, title: 4-(1-Phenylethyl)benzene-1,3-diol; PubChem CID 11171903; downloaded from https://pubchem.ncbi.nlm.nih.gov/compound/11171903, Jan. 13, 2020 (Year: 2020).*
Unknown author, title: 4-(2-Phenylethyl)benzene-1,3-diol; PubChem CID 15664656, downloaded from https://pubchem.ncbi.nlm.nih.gov/compound/4-_2-Phenylethyl_resorcinol; Jan. 13, 2020. (Year: 2020).*
Authors: Jung Won Shin, et al.; title: Current clinical use of depigmenting agents, Dermatologica Sinica, vol. 32, Issue 4, Dec. 2014, pp. 205-210. (Year: 2014).*
Kolbe L, et al; title: 4-n-butylresorcinol, a highly effective tyrosinase inhibitor for the topical treatment of hyperpigmentation; J Eur Acad Dermatol Venereol. Jan. 27, 2013, Suppl 1:19-23. (Year: 2013).*
"Compounds for preventing, reducing and/or alleviating itchy skin conditions(s)," IP.com journal, IP.com Inc., West Henrietta, New York, US, Sep. 13, 2012, pp. 1-110.
"Use of pterocarpans and/or Pao rosa heartwood extract as active anti-irritant and/or anti-oxidant ingredients," IP.com Journal, IP.com Inc., West Henrietta, New York, US, Jan. 4, 2012, pp. 1-40.

* cited by examiner

Primary Examiner — Yanzhi Zhang
(74) Attorney, Agent, or Firm — Dilworth & Barrese, LLP

(57) ABSTRACT

The present invention belongs to the fields of pharmaceuticals and cosmetics, and concerns on the one hand a medicament for the inhibition of and refers also on the cosmetic, non-therapeutic use for the treatment of hyperpigmentation, particularly induced by sun light radiation, preferably induced by visible light radiation.

9 Claims, No Drawings

MEDICAMENT AND COSMETIC COMPOSITION COMPRISING RESORCINOL DERIVATIVES

FIELD OF INVENTION

The present invention belongs to the fields of pharmaceuticals and cosmetics, and concerns on the one hand a medicament for the inhibition of and refers also on the cosmetic, non-therapeutic use for the treatment of hyperpigmentation, particularly induced by sun light radiation, preferably induced by visible light radiation.

STATE OF THE ART

Many people are concerned with the degree of pigmentation of their skin. For example, people with age spots or freckles may wish such pigmented spots to be less pronounced. Others may wish to reduce the skin darkening caused by exposure to sunlight or to lighten their natural skin color. Skin may appear lighter or darker than normal in concentrated areas. Such skin pigmentation disorders occur because the body produces too much or too little melanin, which is the pigment produced by melanocytes in the skin.

Human skin color is determined primarily by the content of the pigment melanin in the basal epidermis layer. Melanin pigments, which are normally brown to black in color, are formed in the melanocytes (pigment-producing cells) of the skin, which are transferred to the keratinocytes and give the skin or hair its color. In mammals, the brown-black eumelanins are primarily formed from hydroxy-substituted aromatic amino acids such as L-tyrosine and L-DOPA, the yellow to red pheomelanins additionally from sulfur-containing molecules (Cosmetics and Toiletries 1996, 111 (5), 43-51). Starting from L-tyrosine, L-3, 4-dihydroxyphenylalanine (L-DOPA) is formed by the copper-containing key enzyme tyrosinase and is in turn converted by tyrosinase to dopachrome. By a series of steps catalysed by various enzymes, the latter is oxidised to form melanin.

The skin can become hyperpigmented when too much melanin concentrates at one area or portion of the skin due to the retention time of the melanosomes in the basal layer. Hyperpigmentation can also occur as a result of overexposure to the sun or due to divers inflammatory stimuli. Increased melanin production is often referred to as melasma, chloasma or solar lentigenes (age spots), solar lentigines ephilides (freckles), and pigmented keratoses. Melasma is a general term describing darkening of the skin. Chloasma is generally used to describe skin discolorations caused by hormones. These hormonal changes are usually the result of pregnancy, birth control pills or estrogen replacement therapy. Solar lentigenes refer to darkened spots on the skin caused by the sun. These spots are quite common in adults with a long history of unprotected sun exposure. The most common cause of darkened areas of skin, brown spots or areas of discoloration is unprotected sun exposure, although hyperpigmentation can also be caused by skin damage, such as blemishes, wounds or rashes.

The prior art discloses ways to treat hyperpigmentation by application of skin lightening agents. Representative skin lightening agents include hydroquinone and Vitamin C. Such agents typically lighten the skin by inhibiting the activity of tyrosinase enzymes involved in melanogenesis.

For instance, EP1206241 A1 relates to methods of lightening skin, e.g., lightening hyperpigmented regions of skin and of lightening skin by regulating melanin in skin by a composition containing certain oxime compounds.

WO 2012 020070 A1 refers to a skin depigmentation composition comprising a meth-imazole derivative, wherein the skin pigmentation disorder is selected from the group consisting of hyperpigmentation, melasma, postinflammatory hyperpigmentation, lentigo, freckles, drug induced hyperpigmentation, light induced hyperpigmentation and chemical induced hyperpigmentation.

According to Duteil L. et al., Differences in visible light-induced pigmentation according to wavelengths: a clinical and histological study in comparison with UVB exposure, Pigment Cell Melanoma Res. 27; 822-826; 2014 John Wiley & Sons A/S; only few studies have been carried out to study visible light effects on skin pigmentation. Duteil et. al. demonstrates that various wavelengths of the visible part of solar spectrum have different effects on skin pigmentation.

The primary object of the present invention was therefore to provide a composition, and method related thereto, for treating, preventing and/or ameliorating sunlight induced, particularly visible light induced hyperpigmentation of skin areas, particularly of human skin. It is another objection of the present invention to provide a synergistic mixture of active ingredients for this purpose, and to provide special formulations for targeted application of the active ingredients.

DESCRIPTION OF THE INVENTION

The subject matter of the invention is a medicament containing at least a resorcinol derivative of formula (I)

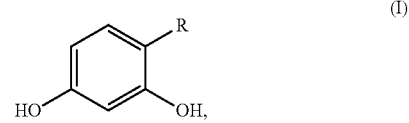

in which R stands for an alkyl radical having 3 to 10 carbon atoms or an optionally substituted alkylphenyl radical having 8 to 16 carbon atoms, for use in the treatment, prevention and/or amelioration of hyperpigmentation.

Resorcinol Derivatives

Resorcinol derivatives of formula (I) are preferably compounds of formula (II)

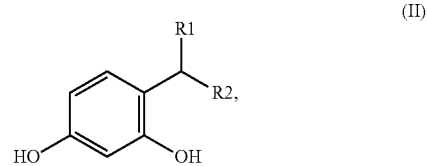

wherein R1 is CH3 or H, and
R2 is a C3-C6 aliphatic residue or the C3-C6 aliphatic residue forms together a ring, which is selected from cyclopropane, cyclobutan, cyclopentan, cyclohexan.

The resorcinol derivatives of the present invention represent well known compounds that can be obtained in the market. Preferably, the compounds are selected from the group consisting of butyl resorcinol, pentyl resorcinol, hexyl resorcinol, heptyl resorcinol, octyl resorcinol, nonyl resorcinol, decylresorcinol, phenylethyl resorcinol, phenylpropyl resorcinol, phenylbutyl resorcinol, phenylhexyl resorcinol, toluoylethyl resorcinol, toluoylpropyl resorcinol, toluoylbutyl resorcinol, toluoylhexyl resorcinol, methoxytoluoylethyl resorcinol, methoxytoluoylpropyl resorcinol, methoxytoluoylbutyl resorcinol, methoxytoluoylhexyl resorcinol, dimethoxytoluoylethyl resorcinol, dimethoxytoluoylpropyl resorcinol, dimethoxytoluoylbutyl resorcinol, dimethoxytoluoylhexyl resorcinol and their mixtures. The preferred compounds are 4-butyl resorcinol, 4-hexyl resorcinol and phenylethyl resorcinol, most preferred is phenylethyl resorcinol (SymWhite® 377).

Surprisingly, it has been observed that resorcinol derivatives as described herein affected the sunlight induced, particularly visible light induced pigmentation of skin areas on which they are applied to, especially in that to prevent, treat and/or ameliorate pigmentation at the area or portion of skin to which they are applied.

In a preferred embodiment the medicament of the present invention is for use in the treatment, prevention and/or amelioration of hyperpigmentation, wherein the hyperpigmentation is induced by the radiation of sunlight, preferably with a wavelength in the range from 100 nm to 1500 nm, preferably 280 nm to 750 nm, more preferably hyperpigmentation which is induced by the radiation of visible light, preferably with a wavelength in the range from 380 nm to 750 nm, more preferably from 400 nm to 700 nm.

Therefore, in the sense of the present invention "hyperpigmentation" is meant to be sunlight induced, more particularly visible light induced hyperpigmentation.

Advantageously the medicament of the present invention is highly effective to prevent, treat and/or ameliorate hyperpigmentation in the said preferred wavelengths, particularly for radiations in the range from 280 nm to 750 nm, particularly for radiations which lie within the visible light wavelengths from 380 nm to 750 nm.

In a preferred embodiment, the medicament of the present invention further comprises at least one UV filters, wherein the UV filters are selected from the group consisting of UV-A filters, UV-B filters, and light protection pigments.

The combination of resorcinol derivatives of formula (I), respectively (II) with UV filters provides synergistically improved prevention, treatment and/or amelioration of hyperpigmentation and thus improves the performance of resorcinol derivatives and conventional UV filters in an unexpected manner, especially in case of 4-butyl resorcinol, 4-hexyl resorcinol and phenylethyl resorcinol, most preferred in case of phenylethyl resorcinol.

UV Filters

Mixtures of resorcinol derivatives of formula (I), respectively (II) and UV filters provide synergistic enhancement of protection of the skin and hair against the harmful effects of sunlight, and thus is advantageously in the treatment, prevention and/or amelioration of hyperpigmentation of human skin, especially in case of 4-butyl resorcinol, 4-hexyl resorcinol and phenylethyl resorcinol, most preferred in case of phenylethyl resorcinol.

Additionally, the combination of resorcinol derivatives of formula (I), respectively (II) and UV filters are well tolerated, not causing reddening, bleaching, or tanning of the skin, are non-irritating, do not dry out the skin, do not form a moist, scaly, powdery, or sticky film, and do not chap the skin when applied to the human skin. These UV filters can be UV-A filters, UV-B filters, pigments, or mixtures thereof that are further explained below, especially in case of 4-butyl resorcinol, 4-hexyl resorcinol and phenylethyl resorcinol, most preferred in case of phenylethyl resorcinol.

UV-A and UV-B Filters

UV filters are understood to refer, for example, to organic substances that are liquid or crystalline at room temperature (light filters) and are capable of absorbing ultraviolet radiation and releasing the absorbed energy in the form of long-wave radiation such as heat. Ordinarily, UV filters are contained in amounts of 0.05 wt % to 50 wt % and preferably 0.5 wt % to 40 wt %. UVB filters can be oil-soluble or water-soluble. Examples of suitable oil-soluble substances include:

3-benzylidene camphor or 3-benzylidene norcamphor and derivatives thereof, such as 3-(4-methylbenzylidene) camphor;

4-aminobenzoic acid derivatives, preferably 4-(dimethylamino)benzoic acid-2-ethyl-hexyl ester, 4-(dimethylamino)benzoic acid-2-octyl ester, and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, and 2-cyano-3,3-phenylcinnamic acid-2-ethylhexyl ester (octocrylene);

esters of salicylic acid, preferably salicylic acid-2-ethylhexyl ester, salicylic acid-4-isopropyl benzyl ester, and salicylic acid homomenthyl ester;

benzophenone derivatives, preferably 2-hydroxy-4-methoxybenzophenone, 2-hydroxy-4-methoxy-4'-methylbenzophenone, and 2,2'-dihydroxy-4-methoxybenzo-phenone;

esters of benzylmalonic acid, preferably 4-methoxybenzylmalonic acid di-2-ethylhexyl ester;

triazine derivatives such as 2,4,6-trianilino-(p-carbo-2'-ethyl-1'-hexyloxy)-1,3,5-triazine and octyl triazone or dioctyl butamidotriazone (Uvasorb® HEB);

propane-1,3-diones such as 1-(4-tert-butylphenyl)-3-(4'-methoxyphenyl)propane-1,3-dione; and ketotricyclo (5.2.1.0) decane derivatives.

Examples of suitable water-soluble substances include:

2-phenylbenzimidazole-5-sulfonic acid and alkali, alkaline earth, ammonium, alkylammonium, alkanolammonium, and glucammonium salts thereof;

1H-benzimidazole-4,6-disulfonic acid, 2,2'-(1,4-phenylene)bis-disodium salt (Neo Heliopan® AP);

sulfonic acid derivatives of benzophenones, preferably 2-hydroxy-4-methoxybenzophenone-5-sulfonic acid and salts thereof;

sulfonic acid derivatives of 3-benzylidene camphor such as 4-(2-oxo-3-bornylidene methyl)benzene sulfonic acid, 2-methyl-5-(2-oxo-3-bornylidene)sulfonic acid, and salts thereof.

Typical examples of particularly suitable UV-A filters include benzoyl methane derivatives such as 1-(4'-tert-butylphenyl)-3-(4'-methoxyphenyl)propane-1,3-dione, 4-tert-butyl-4'-methoxy-dibenzoyl methane (Parsol® 1789), 2-(4-diethylamino-2-hydroxybenzoyl)-benzoic acid hexyl ester (Uvinul® A Plus), 1-phenyl-3-(4'-isopropylphenyl)-propane-1,3-dione, as well as enamine compounds. Of course, the UV-A and UV-B filters can also be used in mixtures. Particularly suitable combinations consist of benzoyl methane derivatives such as 4-tert-butyl-4'-methoxydibenzoyl methane (Parsol® 1789) and 2-cyano-3,3-phenylcinnamic acid-2-ethyl-hexyl ester (octocrylene) in combination with esters of cinnamic acid, preferably 4-methoxycinnamic acid-2-ethylhexyl ester and/or 4-methoxycinnamic acid propyl ester and/or 4-methoxycinnamic acid-isoamyl ester. Such combinations have been advantageously combined with water-soluble filters such as 2-phenylbenzimidazole-5-sulfonic acid and alkali, alkaline earth, ammonium, alkylammonium, alkanolammonium, and glucammonium salts thereof.

In a preferred embodiment the (cosmetic or pharmaceutical) preparation of the present invention comprises at least an additional UV absorbing substance selected from the group consisting of:

3-(4'-trimethylammonium)benzylidenebornan-2-one methyl sulphate
homomenthyl salicylate (Neo Heliopan®HMS)
terephthalylidenedibornanesulphonic acid and salts (Mexoryl®SX)
3-(4'-sulpho)benzylidenebornan-2-one and salts
2-ethylhexyl 2-cyano-3,3-diphenylacrylate (Neo Heliopan®303)
N-[(2 and 4)-[2-(oxoborn-3-ylidene)methyl]benzyl]acrylamide polymer
2-ethylhexyl p-methoxycinnamate (Neo Heliopan®AV)
ethyl p-aminobenzoate (25 mol) ethoxylated
isoamyl p-methoxycinnamate (Neo Heliopan®E1000)
2-phenylbenzimidazole sulfonic acid (Neo Heliopan® Hydro) and its salts
2,4,6-trianilino(p-carbo-2'-ethylhexyl-1'-oxy)-1,3,5-triazine (Uvinul®T150)
phenol,2-(2H-benzotriazol-2-yl)-4-methyl-6-(2-methyl-3 (1,3,3,3-tetramethyl-1-(trimethylsilyl)oxy)disiloxanyl)propyl), (Mexoryl®XL)
4,4'-[(6-[4-(1,1-dimethyl)aminocarbonyl)phenylamino]-1,3,5-triazin-2,4-diyl)-diimino]bis(benzoic acid 2-ethylhexyl ester), (Uvasorb® HEB)
3-(4'-methylbenzylidene)-d,l-camphor (Neo Helipan®MBC)
2-ethylhexyl salicylate (Neo Helipan®OS)
2-ethylhexyl 4-dimethylaminobenzoate (Padimate O)
4-hydroxy-4-methoxybenzophenone-5-sulfonate (Benzophenone-4, Sulisobenzone) and its salts,
benzylidenemalonate-polysiloxane (Parsol®SLX)
menthyl anthranilate (Neo Heliopan®MA)
or mixtures thereof.

In a preferred embodiment, the (cosmetic or pharmaceutical) preparation of the present invention comprises resorcinol derivatives of formula (I), respectively (II) and one, two, three or more UV filters, especially preferred hereby is the combination with 4-butyl resorcinol, 4-hexyl resorcinol or phenylethyl resorcinol with the said UV filters, most preferred is phenylethyl resorcinol.

In a more preferred embodiment the preparation comprises 0.05 wt. % to 0.5 wt. % phenylethyl resorcinol and 0.5 wt. % to 40 wt. % UV filters, and 0.001 wt. % to 98 wt. % additives, wherein all components sum up to 100 wt. %, based on the total amount of the composition.

Light Protection Pigments

In addition to the above-mentioned soluble substances, insoluble light protection pigments, specifically finely-dispersed metal oxides or salts, are also suitable for this purpose. Examples of particularly suitable metal oxides are zinc oxide and titanium dioxide, as well as iron, zirconium, silicon, manganese, aluminum, and cerium oxides and mixtures thereof. Silicates (talc), barium sulfate, or zinc stearate can be used as examples of suitable salts. The oxides and salts are used in the form of pigments for skin care and skin protection emulsions and decorative cosmetics. In this case, the particles should have an average diameter of less than 100 nm, preferably 5 to 50 nm, and particularly preferably 15 to 30 nm. They can be spherical in shape, but particles can also be used that are ellipsoid or whose shape is other than spherical The pigments may also be surface-treated, i.e. in a hydrophilized or hydrophobized form. Typical examples are coated titanium dioxides such as titanium dioxide T 805 (Degussa), Eusolex® T2000, Eusolex® T, Eusolex® T-ECO, Eusolex® T-S, Eusolex® T-Aqua, Eusolex® T-45D (all Merck), and Uvinul TiO$_2$ (BASF). Examples of suitable hydrophobic coating agents in this case are primarily silicones, particularly trialkoxyoctyl silane or simethicone. So-called micro- or nanopigments are preferably used in sun protection agents. Micronized zinc oxides such as Z-COTE® or Z-COTE HP1® are preferably used.

In a preferred embodiment the light protection pigment is selected from microfine titanium dioxide, Zinc oxide, Microfine zinc oxide. When titanium dioxide is chosen as the light protection pigment, it is advantageous that its total amount ranges from 0.1% to 10.0 wt. % of the formulation. When Zinc Oxide is chosen as the light protection pigment it is advantageous that its total amount ranges from 0.1 wt. % to 10.0 wt. % of the formulation and when one or more triazine organic pigment(s) are chosen it is advantageous that its total amount ranges from 0.1% to 10.0 wt. % based on the total amount of the formulation In a preferred embodiment, the medicament of the present invention further comprises at least one skin lightening agent, which is preferably sclareolide.

The combination of resorcinol derivatives of formula (I), respectively (II), preferably 4-butyl resorcinol, 4-hexyl resorcinol or phenylethyl resorcinol, and most preferred phenylethyl resorcinol with skin lightening agent(s) and/or UV filters provide synergistically improved prevention, treatment and/or amelioration of hyperpigmentation and thus improve the performance of resorcinol derivatives of formula (I), respectively (II), preferably 4-butyl resorcinol, 4-hexyl resorcinol or phenylethyl resorcinol, and most preferred phenylethyl resorcinol and conventional skin lightening agents in an unexpected manner, particularly for radiations in the range from 280 nm to 750 nm, particularly for radiations which lie within the visible light wavelengths from 380 nm to 750 nm.

Skin Lighting Agents

Suitable skin lightening agents for the purposes of the present invention encompasses sclareolide, kojic acid derivatives, preferably kojic acid dipalmitate, arbutin, ascorbic acid, ascorbic acid derivatives, preferably magnesium ascorbyl phosphate, hydroquinone, hydroquinone derivatives, cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, *papaya* extract, turmeric extract, mulberry extract, bengkoang extract, nutgrass extract, liquorice root extract or constituents concentrated or isolated therefrom, preferably glabridin or licochalcone A, *artocarpus* extract, extract of *rumex* and *ramulus* species, extracts of pine species (*pinus*), extracts of *vitis* species or stilbene derivatives isolated or concentrated therefrom, saxifrage extract, scutelleria extract, grape extract and/or microalgae extract, in particular *Tetraselmis suecica* Extract.

Preferred skin lightening agents are sclareolide and kojic acid, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, 4-hydroxyanisole, larixol.

Particularly preferred is a combination of resorcinol derivatives of formula (I), respectively (II), preferably 4-butyl resorcinol, 4-hexyl resorcinol or phenylethyl resorcinol, and most preferred phenylethyl resorcinol (SymWhite 377®) with carnosine and/or sclareolide and/or ginger root CO2 extract, which showed the strongest synergistic inhibitory activity towards melanin formation in melanocytes. The ratio of carnosine or sclareolide or ginger root CO2 extracand phenylethyl resorcinol is preferably from 10:90 to 80:20, more preferred from 20:80 to 50:50. Preferably, in case of a mixture of sclareolide, phenylethyl resorcinol (SymWhite 377®) and ginger root CO2 extract, the ratio of the ginger root CO2 extract to phenylethyl resorcinol is from 10:90 to 80:20, preferably 20:80 to 50:50, in which the synergistic inhibitory activity towards melanin formation in melanocytes is strong. Preferred are also preparations comprising resorcinol derivatives of formula (I), respectively (II), preferably 4-butyl resorcinol, 4-hexyl resorcinol or phenylethyl resorcinol, and most preferred phenylethyl resorcinol (SymWhite 377®) and sclareolide and UV filters.

Sclareolide

Sclareolide (CAS Number 564-20-5)

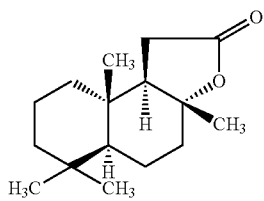

is a compound prepared by chemical modification or by biotransformation of the labdan type diterpene sclareol. Sclareol is present in stems, leaves and flowering parts of clary sage (*Salvia sclarea* L.) and its isolation from this source has been described (U.S. Pat. No. 3,060,172). According to the present invention, the source of sclareolide can be derived (extracted) naturally from either species of the *Salvia* genus, or can be synthetically obtained as substantially pure sclareolide. The substantially pure sclareolide contains according to the present invention more than 70 percent sclareolide.

Synonyms for Sclareolide are (3aR,5aS,9aS,9bR)-decahydro-3a,6,6,9a-tetramethyl-naphtha[2,1-b]furan-2(1H)-one; 3a,4,5,5ac,6,7,8,9,9a,9bα-decahydro-3aβ,6,6,9aβ-tetramethyl-naphtho[2,1-b]furan-2(1H)-one; [3aR-(3aα,5aβ, 9aα,9bβ)]-decahydro-3a,6,6,9a-tetramethyl-Naphtho[2,1-b]furan-2(1H)-one; Norambreinolide; (+)-Norambreinolide; (+)-Sclareolide, (R)-(+)-Sclareolide; 13,14,15,16-Tetranorlabdano-8α,12-lactone; Norambreinolid.

Sclareolide is a precursor of ambroxan, a valuable ambergris fragrance used in perfumery. But as sclareolide is used itself as a fragrance material it is often a component of cosmetic formulations.

The anti-inflammatory activity of sclareol and sclareolide is described in WO 200 230385 A2 (Henkel). The anti-inflammatory activity is proven by an inhibition of 5-lipoxygenase as well as cyclooxygenase-1 activity. The use of Sclareolide within a natural combination of five components to treat acne is given in US 2003 072777 (Color Access). The anti-microbial activity of inter alia sclareolide and sclareol is already described in WO 1999 063978 A1 (Reynolds) concluding that sclareolide and sclareol are useful to treat acne, dermatitis and undesirable body odour. In WO 2001 074327 A2 (Color Access) the use of inter alia sclareolide as cell differentiation enhancer is disclosed. According to this patent the differentiation enhancers like sclareolide are used to stimulate the production of lipids from epidermal cells, and concurrently increase the lipid content of the barrier. As a use of the described compositions the enhancement and prolongation of self-tanning products is mentioned. Again the strengthening of barrier by the use of sclareolide alone as well as combined with white birch extract is described in WO 2002060381 A2 (Color Access). The use of sclareolide in cosmetic formulations used to enhance the stratum corneum function is described in US 2010 247692 A1 (Color Access). The invention WO 2008 155048 A1 (Cognis) discloses cosmetic compositions comprising sclareolide alone or combined with hesperidin methyl chalcone. The cosmetic compositions are described to be used for the tanning of skin, the darkening of hair, or the preventing of greying of hair.

Ginger Root CO2 Extract

Ginger root extracts with a high content of pungent components are well-known for the flavouring of food and beverages. The characterization of ginger root extracts by HPLC, GC and other analytical methods is well-described. The quantification of pungent components like gingerols, shogaols and zingerone is good laboratory practice. But ginger extracts characterized by a high content of pungent components of 42-50% b.w. have not been described for cosmetic applications before.

The water and/or ethanol and/or water/ethanol extracts of ginger root of unknown composition are described as antioxidants and anti-aging agents and are often disclosed as the preferred extracts for these applications. The use of these extracts is described inter alia in JP 2009 073777 A1 for the improvement of wrinkles, in JP 2000 319189 A1 as elastase inhibitors, by Fujimura et al. (Fragrance Journal (2002), 30(6), 38-42) for wrinkle improvement by inhibition of elastase activity. In JP 2007008847 the claimed extract was prepared with 20% ethanol resulting in the concentration of fructosyl dipeptides as active principles.

For the application to hair and scalp ginger tincture, ginger juice and the above mentioned water and/or ethanol and/or water/ethanol extracts of ginger root are well-known. As activities for these extracts on hair and scalp inter alia enhanced microcirculation is described. For example, CN 102451128 A1 suggests a shampoo claimed to prevent hair loss contains 5% ginger juice. JP 63 091315 A1 describes microcirculation enhancing ginger juice in shampoo formations for hair growth stimulation. EP 1281402 B1 (Kao) refers to a ginger extract substantially free of gingerols for hair growth inhibition.

Ginger oil was used as a soothing, relaxing or warming agent in cosmetic formulations in WO 2009 087578 A1 (Foamix). But the document did not disclose the composition of the ginger oil. The essential oil of ginger is known for a strong pungent smell and taste due to the volatile constituents and is not comparable to the ginger pungent extract according to the present invention.

The isolation of the pungent components of ginger is described in different documents. Ficker et al. (Phytotherapy Research (2003), 17(8), 897-902) evaluated the anti-fungal activity of ginger constituents.

The evaluation of anti-inflammatory activity of pungent components of ginger was given in different documents, inter alia by Lantz et al. (Phytomedicine (2007), 14(2-3), 123-128). Additionally the anti-tumour activity and proliferation inhibitory activity on tumour cells were evaluated by different groups, inter alia by Sang et al. (Journal of Agricultural and Food Chemistry (2009), 57(22), 10645-10650).

In CN 1840162 A1 a ginger root $CO_2$ extract is described without specifying the content of pungent components like gingerols and shogaols. The extract is disclosed as an anti-inflammatory extract. Application examples are tablets, pills and capsules for oral consumption. Examples for topical application on skin are not described.

Ginger root CO2 extracts that are particularly preferred in combination with resorcinol derivatives of formula (I), respectively (II), preferably 4-butyl resorcinol, 4-hexyl resorcinol or phenylethyl resorcinol, and most preferred phenylethyl resorcinol (SymWhite 377®) in the sense of the present invention contain

| (a) | 15 to 30 | % b.w. [6]-gingerol |
| (b) | 3 to 10 | % b.w. [8]-gingerol |
| (c) | 3 to 10 | % b.w. [10]-gingerol |
| (d) | 0.5 to 4 | % b.w. [6]-shogaol |
| (e) | 0.03 to 1.3 | % b.w. [8]-shogaol; |
| (f) | 0.03 to 1 | % b.w. [10]-shogaol; |
| (g) | 0.01 to 1 | % b.w. zingerone, | on condition that the amount of gingerols sums up to 24 to 50% b.w. and the amount of shogaols sums up to 0.5 to 6% b.w.

A first preferred ginger root CO2 extract comprises

| (a) | 25 to 30 | % b.w. [6]-gingerol |
| (b) | 5 to 10 | % b.w. [8]-gingerol |
| (c) | 5 to 10 | % b.w. [10]-gingerol |
| (d) | 1.5 to 4 | % b.w. [6]-shogaol |
| (e) | 0.3 to 1.3 | % b.w. [8]-shogaol; |
| (f) | 0.03 to 1 | % b.w. [10]-shogaol; |
| (g) | 0.01 to 1 | % b.w. zingerone, | on condition that the amount of gingerols sums up to 35 to 50% b.w. and the amount of shogaols sums up to 1.5 to 6% b.w. Extracts of this kind are subject to EP 2772245 A1 (SYMRISE) which is hereby incorporated by reference with regard to the nature of the extracts and the manner how to obtain them. The product is obtainable under the trademark SymVital® AgeRepair 3040 from Symrise AG, Holzminden (DE).

A second preferred ginger root CO2 extract comprises

| (a) | 15 to 25 | % b.w. [6]-gingerol |
| (b) | 3 to 5 | % b.w. [8]-gingerol |
| (c) | 3 to 8 | % b.w. [10]-gingerol |
| (d) | 0.5 to 3 | % b.w. [6]-shogaol |
| (e) | 0.03 to 1 | % b.w. [8]-shogaol; |
| (f) | 0.03 to 1 | % b.w. [10]-shogaol; |
| (g) | 0.01 to 1 | % b.w. zingerone, | on condition that the amount of gingerols sums up to 24 to 35% b.w. and the amount of shogaols sums up to 0.5 to 5% b.w.

Carriers

Both the medicaments and the cosmetic preparations described in the following can contain as component (c) carriers or solvents that are selected from the group selected consisting of water, alcohols, esters, butylene glycol, dipropylene glycol, pentylene glycol, 1,2-hexane diol, caprylyl glycol, decylene glycol, ethanol, ethoxydiglycol, ethyl acetate, glycerol, propanol, isopropanol, macrogols, propyl propylene glycol(2) methyl ether, propyl propylene glycol (3) methyl ether, propylene carbonate, propylene glycol, triethylene glycol, isoparaffin, amyl acetate, amyl benzoate, benzyl acetate, butyl acetate, butylene glycol, butyl lactate, butooctyl benzoate, butooctyl salicylate, C10-C13 alkanes, C14-C17 alkanes, C11-C15 cycloalkanes, caprylyl butyrate, isoparaffins, diacetin, triacetin dicaprylyl ether, dicaprylyl maleate, and mixtures thereof. Most preferred are glycerol, propylene glycol, butylene glycol, dipropylene glycol, pentylene glycol, 1,2-hexane diol, caprylyl glycol, decylene glycolas compound c) of a medicament preparation of the present invention.

The matter of the present invention lies on the boundary area between medicaments and cosmetics, particularly as a sun protection agent. Therefore, in the following medicament as well as cosmetic preparations are described.

Medicament

A preferred medicament of the present invention comprises, consists or essentially consists of:

(a) from 0.01 wt. % to 10 wt. %, preferably from 0.02 wt. % to 2 wt. %, particularly preferably from 0.05 wt. % to 1 wt % at least one resorcinol derivative of formula (I), respectively (II), preferably 4-butyl resorcinol, 4-hexyl resorcinol or phenylethyl resorcinol, and most preferred phenylethyl resorcinol (SymWhite 377®) or a pharmaceutically acceptable salt of resorcinol derivatives of formula (I), respectively (11), preferably 4-butyl resorcinol, 4-hexyl resorcinol or phenylethyl resorcinol, and most preferred phenylethyl resorcinol, (b) and at least one compound selected from (b1), (b2) and (b3):

(b1) from 0.05 wt. % to 60 wt. %, preferably 0.1 to 50 wt. %, particularly preferably 0.5 wt. % to 40 wt % of UV filters, (b2) from 0.005 wt. % to 20 wt. %, preferably 0.01 wt. % to 10 wt. % of skin lightening agents, (b3) from 0.0001 wt. % to 30 wt. %, preferably 0.01 wt. % to 10 wt. % of antioxidants, and optionally (c) from 0.2 wt. % to 99 wt. %, preferably from 0.5 wt. % to 20 wt. %, particularly preferably from 1 wt. % to 10 wt. % of carriers, and/or (d) 0.1 wt. % to 90 wt. % further additives, wherein the weight percents of the compounds a) to d) are based on the total amount of the preparation and the sum of all compounds add to 100 wt. %.

The medicament according to the invention preferably contains, respectively essentially consists of components (a) and (b1) in a weight ratio of 0.02:99.98 to 99.5:0.5, particularly 0.04:99.96 to 95:5, and particularly preferably 0.2:99.8 to 75:25. The synergistic effect is most pronounced when the two components are used in a weight ratio of 1:80.

The medicaments according to the invention preferably contain, respectively essentially consist of components (a) and (b2) in a weight ratio of 0.05:99.95 to 99.95:0.05, and particularly preferably 1:99 to 99:1. The synergistic effect is most pronounced when the two components are used in a weight ratio of 5:1 to 1:5.

The medicaments according to the invention preferably contain, respectively essentially consist of components (a) and (b3) in a weight ratio of 0.05:99.95 to 99.95:0.05, and particularly preferably 1:99 to 99:1. The synergistic effect is most pronounced when the two components are used in a weight ratio of 5:1 to 1:5.

Preference is made to a medicament comprising or consisting of or essentially consisting of:
(a) from 0.01 wt. % to 10 wt. %, preferably from 0.02 wt. % to 2 wt. %, particularly preferably from 0.05 wt. % to 1 wt % of at least one resorcinol derivative of formula (I), respectively (II), preferably 4-butyl resorcinol, 4-hexyl resorcinol or phenylethyl resorcinol, and most preferred phenylethyl resorcinol (SymWhite 377®) or a pharmaceutically acceptable salt of resorcinol derivatives of formula (I), respectively (II), preferably 4-butyl resorcinol, 4-hexyl resorcinol or phenylethyl resorcinol, and most preferred phenylethyl resorcinol, and
(b1) from 0.05 wt. % to 60 wt. %, preferably 0.1 to 50 wt. %, and particularly preferably 0.5 wt. % to 40 wt % of UV filters, and
(b3) from 0.0001 wt. % to 30 wt. %, preferably 0.01 wt. % to 10 wt. % of antioxidants, and
(c) from 0.2 wt. % to 99 wt. %, preferably from 0.5 wt. % to 20 wt. %, and particularly preferably from 1 wt. % to 10 wt. % of carriers selected from the group composed of water, alcohols, esters, butylene glycol, dipropylene glycol, ethanol, ethoxydiglycol, ethyl acetate, glycerol, propanol, isopropanol, macrogols, propyl propylene glycol (2) methyl ether, propyl propylene glycol(3) methyl ether, propylene carbonate, propylene glycol, triethylene glycol, isoparaffin, amyl acetate, amyl benzoate, benzyl acetate, butyl acetate, butylene glycol, butyl lactate, butooctyl benzoate, butooctylsalicylate, C10-C13 alkanes, C11-C15 cycloalkanes, caprylyl butyrate, isoparaffins, diacetin, triacetin dicaprylyl ether, dicaprylyl maleate, and mixtures thereof,
 most preferred are glycerol, propylene glycol, butylene glycol, dipropylene glycol, pentylene glycol, 1,2-hexane diol, caprylyl glycol, decylene glycole, and mixtures thereof, and
(d) 0.1 to 90 wt. % further additives,
wherein the weight percents of the compounds a) to d) are based on the total amount of the preparation and the sum of all compounds add to 100 wt. %.

A further preferred medicament comprises or consists of or essentially consists of:
(a) from 0.01 wt. % to 10 wt. %, preferably from 0.02 wt. % to 2 wt. %, particularly preferably from 0.05 wt. % to 1 wt % of at least one resorcinol derivative of formula (I), respectively (II), preferably 4-butyl resorcinol, 4-hexyl resorcinol or phenylethyl resorcinol, and most preferred phenylethyl resorcinol (SymWhite 377®) or a pharmaceutically acceptable salt of resorcinol derivatives of formula (I), respectively (II), preferably 4-butyl resorcinol, 4-hexyl resorcinol or phenylethyl resorcinol, and most preferred phenylethyl resorcinol, and
(b1) from 0.05 wt. % to 60 wt. %, preferably 0.1 to 50 wt. %, and particularly preferably 0.5 wt. % to 40 wt % of UV filters, and
(b2) from 0.005 wt. % to 20 wt. %, preferably from 0.01 wt. % to 10 wt. % of skin lightening agents, and
(c) from 0.2 wt. % to 99 wt. %, preferably from 0.5 wt. % to 20 wt. %, and particularly preferably from 1 wt. % to 10 wt. % of carriers selected from the group composed of water, alcohols, esters, butylene glycol, dipropylene glycol, ethanol, ethoxydiglycol, ethyl acetate, glycerol, propanol, isopropanol, macrogols, propyl propylene glycol (2) methyl ether, propyl propylene glycol(3)-methyl ether, propylene carbonate, propylene glycol, triethylene glycol, isoparaffin, amyl acetate, amyl benzoate, benzyl acetate, butyl acetate, butylene glycol, butyl lactate, butooctyl benzoate, butooctylsalicylate, C10-C13 alkanes, C14-C17 alkanes, C11-C15 cycloalkanes, caprylyl butyrate, isoparaffins, diacetin, triacetin dicaprylyl ether, dicaprylyl maleate, and mixtures thereof, most preferred are glycerol, propylene glycol, butylene glycol, dipropylene glycol, pentylene glycol, 1,2-hexane diol, caprylyl glycol, decylene glycole, and mixtures thereof, and
(d) 0.1 to 90 wt. % further additives,
wherein the weight percent of the compounds a) to d) are based on the total amount of the preparation and the sum of all compounds add to 100 wt. %.

A further preferred medicament comprises or consists of or essentially consists of:
(a) from 0.01 wt. % to 10 wt. %, preferably from 0.02 wt. % to 2 wt. %, particularly preferably from 0.05 wt. % to 1 wt % of at least one resorcinol derivative of formula (I), respectively (II), preferably 4-butyl resorcinol, 4-hexyl resorcinol or phenylethyl resorcinol, and most preferred phenylethyl resorcinol (SymWhite 377®) or a pharmaceutically acceptable salt of resorcinol derivatives of formula (I), respectively (II), preferably 4-butyl resorcinol, 4-hexyl resorcinol or phenylethyl resorcinol, and most preferred phenylethyl resorcinol, and
(b1) from 0.05 wt. % to 60 wt. %, preferably 0.1 to 50 wt. %, and particularly preferably 0.5 wt. % to 40 wt % of UV filters, wherein the UV filters are UV absorbing substances selected from the group consisting of:
3-(4'-trimethylammonium)benzylidenebornan-2-one methyl sulphate
homomenthyl salicylate (Neo Heliopan®HMS)
terephthalylidenedibornanesulphonic acid and salts (Mexoryl®SX)
3-(4'-sulpho)benzylidenebornan-2-one and salts
2-ethylhexyl 2-cyano-3,3-diphenylacrylate (Neo Heliopan®303)
N-[(2 and 4)-[2-(oxoborn-3-ylidene)methyl]benzyl]acrylamide polymer
2-ethylhexyl p-methoxycinnamate (Neo Heliopan®AV)
ethyl p-aminobenzoate (25 mol) ethoxylated
isoamyl p-methoxycinnamate (Neo Heliopan®E1000)
2-phenylbenzimidazole sulfonic acid (Neo Heliopan® Hydro) and its salts
2,4,6-trianilino(p-carbo-2'-ethylhexyl-1'-oxy)-1,3,5-triazine (Uvinul®T150)
phenol,2-(2H-benzotriazol-2-yl)-4-methyl-6-(2-methyl-3 (1,3,3,3-tetramethyl-1-(trimethylsilyl)oxy)disiloxanyl)propyl), (Mexoryl®XL)
4,4'-[(6-[4-(1,1-dimethyl)aminocarbonyl)phenylamino]-1,3,5-triazin-2,4-diyl)-diimino]bis(benzoic acid 2-ethylhexyl ester), (Uvasorb® HEB)

3-(4'-methylbenzylidene)-d,l-camphor (Neo Helipan®MBC)
2-ethylhexyl salicylate (Neo Helipan®OS)
2-ethylhexyl 4-dimethylaminobenzoate (Padimate O)
4-hydroxy-4-methoxybenzophenone-5-sulfonate (Benzophenone-4, Sulisobenzone) and its salts,
benzylidenemalonate-polysiloxane (Parsol®SLX)
menthyl anthranilate (Neo Heliopan®MA), and (b2) from 0.005 wt. % to 20 wt. %, preferably from 0.01 wt. % to 10 wt. % of skin lightening agents, preferably selected from kojic acid, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, 4-hydroxyanisole, sclareolide, larixol; most preferred is sclareolide, (b3) from 0.0001 wt. % to 30 wt. %, preferably 0.01 wt. % to 10 wt. % of antioxidants, preferably selected from amino acids (such as glycine, histidine, tyrosine, tryptophan), imidazoles (such as urocanic acid), carotenoids, carotenes (such as (α-carotene, β-carotene, lycopene), chlorogenic acids, liponic acids (such as dihydroliponic acid), auro-thioglucose, propylthiouracil and other thiols (such as thioredoxin, glutathione, cysteine, cystine, cystamine and glycosyls thereof, N-acetyl, methyl, ethyl, propyl, amyl, butyl and lauryl, palmitoyl, oleyl, γ-linoleyl, cholesteryl and glyceryl esters), dilauryl thiodipropionate, distearyl thiodipropionate, thiodipropionic acids and derivatives thereof (esters, ethers, peptides, lipids, nucleotides, nucleosides and salts), as well as sulfoximine compounds (such as buthionine sulfoximine, homocysteine sulfoximine, buthionine sulfone, penta, hexa, heptathionine sulfoximine), as well as (metal) chelators (such as α-hydroxy fatty acids, palmitic acid, phytic acid, and lactoferrin), α-hydroxy acids (such as citric acid, lactic acid, and malic acid), humic acid, gallic acid, gall extracts, bilirubin, biliverdin, EDTA, EGTA and derivatives thereof, unsaturated fatty acids (such as γ-linolenic acid, linoleic acid, and oleic acid), folic acid and derivatives thereof, ubiquinone, ubiquinol and derivatives thereof, Vitamin C and derivatives thereof (such as ascorbyl palmitate, Mg ascorbyl phosphate, ascorbyl acetate), tocopherols and derivatives thereof (such as Vitamin E acetate), Vitamin A and derivatives thereof (vitamin A palmitate), as well as coniferyl benzoate of benzoin, rutic acid and derivatives thereof, α-glycosylrutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, [6]-Paradol (INCI: Hydroxymethoxyphenyl Decanone), carnosine, L-carnosine, D-carnosine, D/L-carnosine, carcinine, carcinine*HCl (INCI: decarboxy carnosine*HCl), anserine, D-anserine, L-anserine, as well as L-anserine*HNO$_3$ and mixtures thereof; and (c) from 0.2 wt. % to 99 wt. %, preferably from 0.5 wt. % to 20 wt. %, and particularly preferably from 1 wt. % to 10 wt. % of carriers selected from the group consisting of water, alcohols, esters, butylene glycol, dipropylene glycol, ethanol, ethoxydiglycol, ethyl acetate, glycerol, propanol, isopropanol, macrogols, propyl propylene glycol (2) methyl ether, propyl propylene glycol(3) methyl ether, propylene carbonate, propylene glycol, triethylene glycol, isoparaffin, amyl acetate, amyl benzoate, benzyl acetate, butyl acetate, butylene glycol, butyl lactate, butooctyl benzoate, butooctylsalicylate, C10-C13 alkanes, C14-C17 alkanes, C11-C15 cycloalkanes, caprylyl butyrate, isoparaffins, diacetin, triacetin dicaprylyl ether, dicaprylyl maleate, and mixtures thereof, most preferred are glycerol, propylene glycol, butylene glycol, dipropylene glycol, pentylene glycol, 1,2-hexane diol, caprylyl glycol, decylene glycole, and mixtures thereof; and (d) 0.1 to 90 wt. % further additives, wherein the weight percent of the compounds a) to d) are based on the total amount of the preparation and the sum of all compounds add to 100 wt. %.

A further preferred medicament comprises or consists of or essentially consists of:

(a) from 0.01 wt. % to 10 wt. %, preferably from 0.02 wt. % to 2 wt. %, and particularly preferably from 0.05 wt. % to 1 wt % of at least one resorcinol derivative of formula (I), respectively (II), preferably 4-butyl resorcinol, 4-hexyl resorcinol or phenylethyl resorcinol, and most preferred phenylethyl resorcinol (SymWhite 377®) or a pharmaceutically acceptable salt of resorcinol derivatives of formula (I), respectively (II), preferably 4-butyl resorcinol, 4-hexyl resorcinol or phenylethyl resorcinol, and most preferred phenylethyl resorcinol, and (b1) from 0.05 wt. % to 60 wt. %, preferably 0.1 to 50 wt. %, and particularly preferably 0.5 wt. % to 40 wt % of UV filters, wherein the UV filters are UV absorbing substances selected from the group consisting of:

3-(4'-trimethylammonium)benzylidenebornan-2-one methyl sulphate homomenthyl salicylate (Neo Heliopan®HMS)

terephthalylidenedibornanesulphonic acid and salts (Mexoryl®SX)

3-(4'-sulpho)benzylidenebornan-2-one and salts 2-ethylhexyl 2-cyano-3,3-diphenylacrylate (Neo Heliopan®303)

N-[(2 and 4)-[2-(oxoborn-3-ylidene)methyl]benzyl]acrylamide polymer 2-ethylhexyl p-methoxycinnamate (Neo Heliopan®AV)

ethyl p-aminobenzoate (25 mol) ethoxylated isoamyl p-methoxycinnamate (Neo Heliopan®E1000)

2-phenylbenzimidazole sulfonic acid (Neo Heliopan® Hydro) and its salts 2,4,6-trianilino(p-carbo-2'-ethylhexyl-1'-oxy)-1,3,5-triazine (Uvinul®T150)

phenol,2-(2H-benzotriazol-2-yl)-4-methyl-6-(2-methyl-3 (1,3,3,3-tetramethyl-1-(trimethylsilyl)oxy)disiloxanyl)propyl), (Mexoryl®XL)

4,4'-[(6-[4-(1,1-dimethyl)aminocarbonyl)phenylamino]-1,3,5-triazin-2,4-diyl)-diimino]bis(benzoic acid 2-ethylhexyl ester), (Uvasorb® HEB)

3-(4'-methylbenzylidene)-d,l-camphor (Neo Helipan®MBC)

2-ethylhexyl salicylate (Neo Helipan®OS)

2-ethylhexyl 4-dimethylaminobenzoate (Padimate O)

4-hydroxy-4-methoxybenzophenone-5-sulfonate (Benzophenone-4, Sulisobenzone) and its salts, benzylidenemalonate-polysiloxane (Parsol®SLX)

menthyl anthranilate (Neo Heliopan®MA), and (b2) from 0.005 wt. % to 20 wt. %, preferably from 0.01 wt. % to 10 wt. % of skin lightening agents, preferably selected from kojic acid, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, 4-hydroxyanisole, sclareolide, larixol; most preferred is sclareolide; and (b3) from 0.0001 wt. % to 30 wt. %, preferably 0.01 wt. % to 10 wt. % of antioxidants, preferably selected from amino acids (such as glycine, histidine, tyrosine, tryptophan), imidazoles (such as urocanic acid), carotenoids, carotenes (such as (α-carotene, β-carotene, lycopene), chlorogenic acids, liponic acids (such as dihydroliponic acid), auro-thioglucose, propylthiouracil, dilauryl thiodipropionate, distearyl thiodipropionate, thiodipropionic acids and derivatives thereof (esters, ethers, peptides, lipids, nucleotides, nucleosides and salts), as well as sulfoximine compounds (such as buthionine sulfoximine, homocysteine sulfoximine, buthionine sulfone, penta, hexa, heptathionine sulfoximine), citric acid, lactic acid, and malic acid), humic acid, gallic acid, gall extracts, bilirubin, biliverdin, EDTA, EGTA γ-linolenic acid, linoleic acid, and oleic acid, folic acid ubiquinone, ubiquinol Vitamin C ascorbyl palmitate, Mg ascorbyl phosphate, ascorbyl acetate), tocopherols Vitamin E acetate, Vitamin A, vitamin A palmitate, α-glycosylrutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, [6]-Paradol (INCI: Hydroxymethoxyphenyl Decanone), carnosine, L-carnosine, D-carnosine, D/L-carnosine, carcinine, carcinine*HCl (INCI: decarboxy carnosine*HCl), anserine, D-anserine, L-anserine, as well as L-anserine*HNO$_3$ and mixtures thereof; and (c) from 0.2 wt. % to 99 wt. %, preferably from 0.5 wt. % to 20 wt. %, and particularly preferably from 1 wt. % to 10 wt. % of carriers selected from the group consisting of water, alcohols, esters, butylene glycol, dipropylene glycol, ethanol, ethoxydiglycol, ethyl acetate, glycerol, propanol, isopropanol, macrogols, propyl propylene glycol (2) methyl ether, propyl propylene glycol(3) methyl ether, propylene carbonate, propylene glycol, triethylene glycol, isoparaffin, amyl acetate, amyl benzoate, benzyl acetate, butyl acetate, butylene glycol, butyl lactate, butooctyl benzoate, butooctylsalicylate, C10-C13 alkanes, C14-C17 alkanes, C11-C15 cycloalkanes, caprylyl butyrate, isoparaffins, diacetin, triacetin dicaprylyl ether, dicaprylyl maleate, and mixtures thereof, most preferred are glycerol, propylene glycol, butylene glycol, dipropylene glycol, pentylene glycol, 1,2-hexane diol, caprylyl glycol, decylene glycole, and mixtures thereof, and (d) 0.05 to 5 wt. % multifunctionals, which are selected from the group consisting of 1,3-propanediol, methyl propanediol, 1,2-pentanediol, 1,2-hexanediol, 1,2-octanediol, 1,2-decanediol, 1,5-pentanediol, 1,6-hexanediol, 1,8-octanediol, 1,2-decanediol, ethylhexylglycerin, hexoxy-propan-1,2-diol, heptoxy-propan-1,2-diol, octoxy-propan-1,2-diol, 3-phenoxy-propan-1,2-diol, 3-benzyloxy-propan-1,2-diol, 3-phenylethyloxy-propan-1,2-diol, 3-phenylpropyloxy-propan-1,2-diol, 3-methylbenzyloxy-propan-1,2-diol, sorbitan caprylate, triclosan, climbazole, Octopirox (1-hydroxy-4-methyl-6-(2,4,4-trimethylpentyl)-2(1H)-pyridone, 2-aminoethanol), chitosan, farnesol, 2-butyloctanoic acid, 2-Benzylheptan-1-ol, glycerol monolaurate, bis(2-pyridylthio)zinc 1,1'-dioxide, N,N'-(decane-1,10-diyldipyridin-1-yl-4-ylidene)-dioctan-1-amine dihydrochloride (octenidine dihydrochloride), thymol, eugenol, 4-isopropyl-3-methylphenol, benzyl alcohol, 2-phenyethyl alcohol, 3-phenyl propanol, 2-phenoxyethanol, 1-phenoxy-propan-2-ol, 3-phenoxypropanol, benzyloxymethanol, glyceryl caprylate, glyceryl caprate, glyceryl laurate, hydroxyacetophenone, and mixtures thereof, preferably which are selected from 2-pentanediol, 1,2-hexanediol, 1,2-octanediol, 1,2-decanediol, hydroxyacetophenone, and mixtures thereof, wherein the weight percents of the compounds a) to d) are based on the total amount of the preparation and the sum of all compounds add to 100 wt. %.

Most preferred is a medicament comprising or consisting of or essentially consisting of a combination of at least one resorcinol derivative of formula (I), respectively (II), preferably 4-butyl resorcinol, 4-hexyl resorcinol or phenylethyl resorcinol, and most preferred phenylethyl resorcinol (SymWhite 377®) with at least a further compound (b1), (b2) or (b3) which are preferably selected from ginger root CO2 extract, carnosine, L-carnosine, D-carnosine, D/L-carnosine, carcinine, carcinine*HCl (INCI: decarboxy carnosine*HCl), anserine, D-anserine, L-anserine, as well as L-anserine*HNO$_3$, sclareolide, larixol. Preferably, two, three or more of the aforementioned compounds are present in a medicament of the present invention.

Most preferred is a binary mixture comprising, consisting or essentially consisting of a resorcinol derivative of formula (I), respectively (II), preferably 4-butyl resorcinol, 4-hexyl resorcinol or phenylethyl resorcinol, and most preferred phenylethyl resorcinol (SymWhite 377®) with ginger root CO2 extract. In such a binary mixture ginger root CO2 extract is preferably present in an amount from 5% by weight to 80% by weight, and phenylethyl resorcinol and phenylethyl resorcinol derivatives preferably present in an amount from 20% by weight to 95% by weight, with the provision that all actives add together to 100% by weight.

Another preferred mixture is a binary mixture comprising, consisting or essentially consisting of a resorcinol derivative of formula (I), respectively (II), preferably 4-butyl resorcinol, 4-hexyl resorcinol or phenylethyl resorcinol, and most preferred phenylethyl resorcinol (SymWhite 377®) with carnosine, wherein carnosine is preferably present in an amount from 5% by weight to 80% by weight, and phenylethyl resorcinol and phenylethyl resorcinol derivatives are preferably present in an amount from 20% by weight to 95% by weight, with the provision that all actives add together to 100% by weight.

Another preferred mixture is a ternary mixture comprising, consisting or essentially consisting of a resorcinol derivative of formula (I), respectively (II), preferably 4-butyl resorcinol, 4-hexyl resorcinol or phenylethyl resorcinol, and most preferred phenylethyl resorcinol (SymWhite 377®) with ginger root CO2 extract and sclareolide.

Preferably ginger root CO2 extract is present in an amount from 5% by weight to 70% by weight, wherein sclareolide is preferably present in an amount from 5% by weight to 70% by weight, and resorcinol derivative of formula (I), respectively (II), preferably 4-butyl resorcinol, 4-hexyl resorcinol or phenylethyl resorcinol, and most preferred phenylethyl resorcinol (SymWhite 377®) is preferably present in an amount from 10% by weight to 90% by weight in such a ternary mixture, with the provision that all three compounds add together to 100% by weight.

Another preferred mixture is a ternary mixture comprising a resorcinol derivative of formula (I), respectively (II), preferably 4-butyl resorcinol, 4-hexyl resorcinol or phenylethyl resorcinol, and most preferred phenylethyl resorcinol (SymWhite 377®) and ginger root CO2 extract and carnosine.

Preferably ginger root CO2 extract is present in an amount from 5% by weight to 70% by weight, wherein the resorcinol derivative of formula (I), respectively (II), preferably 4-butyl resorcinol, 4-hexyl resorcinol or phenylethyl resorcinol, and most preferred phenylethyl resorcinol (SymWhite 377®) is preferably present in an amount from 10% by weight to 90% by weight and carnosine is preferably present in an amount from 5% by weight to 70% by weight in such a ternary mixture, with the provision that all three compounds add together to 100% by weight.

Cosmetic Preparations

A preferred cosmetic preparation of the present invention comprises, consists or essentially consists of:
(a) at least a resorcinol derivative of formula (I), respectively (II), preferably 4-butyl resorcinol, 4-hexyl resorcinol or phenylethyl resorcinol, and most preferred phenylethyl resorcinol (SymWhite 377®) or a pharmaceutically acceptable salt thereof,
and at least one compound selected from (b1), (b2) and (b3):
(b1) at least one UV filters,
(b2) at least one skin lightening agent,
(b3) at least an antioxidant,
and at least one compound selected from (c1), (c2) and (c3):
(c1) carriers,
(c2) oil components
(c3) emulsifiers,
preferably for use in the treatment, prevention and/or amelioration of hyperpigmentation.

In terms of the UV filters, skin lightening agents, antioxidants and carriers the aforementioned disclosure and preference under medicaments also applies here for the cosmetic preparations and use and are therefore incorporated herewith.

A preferred cosmetic preparation comprises, consists or essentially consists of
(a) from 0.01 wt. % to 10 wt. %, preferably from 0.02 wt. % to 2 wt. %, and particularly preferably from 0.05 wt. % to 1 wt. % of at least one resorcinol derivative of formula (I), respectively (II), preferably 4-butyl resorcinol, 4-hexyl resorcinol or phenylethyl resorcinol, and most preferred phenylethyl resorcinol (SymWhite 377®) or a cosmetically acceptable salt thereof;
and at least one compound selected from (b1), (b2) and (b3):
(b1) from 0.05 wt. % to 60 wt. %, preferably 0.1 to 50 wt. %, and particularly preferably 0.5 wt. % to 40 wt % of UV filters,
(b2) from 0.005 wt. % to 20 wt. %, preferably from 0.01 wt. % to 10 wt. % of skin lightening agents,
(b3) from 0.0001 wt. % to 30 wt. %, preferably 0.5 wt. % to 20 wt. % of antioxidants, and at least one compound selected from (c1), (c2) and (c3):
(c1) carriers,
(c2) oil components,
(c3) emulsifiers,
wherein the total amount of the compounds (c1) to (c3) sum up together to be iwt. % to 50 wt. %, preferably 5 wt. % to 40 wt % relative to the preparation, and wherein the total weight percent of the compounds (a) to (c1 to c3) are based on the total amount of the preparation and the sum of all compounds (a), (b), (c) add to 100 wt. %.

The preparations according to the invention are preferably in the form of creams, lotions, gels, pastes, or capsules, and particularly constitute skin care agents, sun protection agents, or hair care agents.

It is further preferred that components (a+b1) be present in an amount of 0.1 wt. % to 40 wt. % relative to the entire composition. In this case, the same preferred weight ratios described above apply.

It is further preferred that components (a+b2) be present in an amount of 0.1 wt. % to 10 wt. % relative to the entire composition. In this case, the same preferred weight ratios described above apply.

It is further preferred that components (a+b3) be present in an amount of 0.05 wt. % to 10 wt. % relative to the entire composition. In this case, the same preferred weight ratios described above apply.

The resorcinol derivative of formula (I), respectively (II), preferably 4-butyl resorcinol, 4-hexyl resorcinol or phenylethyl resorcinol, and most preferred phenylethyl resorcinol (SymWhite 377®) is present in the medicament, respectively cosmetic preparation of use in an active amount to reduce, retard, suppress and/or protect against sunlight induced hyperpigmentation, particularly visible light induced hyperpigmentation.

The term "active amount" to reduce, retard and/or suppress hyperpigmentation, respectively to treat, prevent and/or ameliorate hyperpigmentation of skin area, preferably of human skin refers to a mean amount sufficient to cover the region of skin surface where a change in pigmentation is desired, particularly preferably used for radiation wavelengths in the range from 380 nm to 750 nm, more preferably from 400 nm to 700 nm in case of the visible light radiations.

In a preferred method for cosmetic and/or therapeutic reduction, retardation and/or suppression, respectively treatment, prevention and/or amelioration of hyperpigmentation, the concentration in which resorcinol derivative of formula (I), respectively (II), preferably 4-butyl resorcinol, 4-hexyl resorcinol or phenylethyl resorcinol, and most preferred phenylethyl resorcinol (SymWhite 377®) is used in an "active amount" according to the invention is in the range from 0.01 wt. % to 10 wt. % preferably in the range from 0.02 wt. % to 2 wt. % and particularly preferentially in the range from 0.05 wt. % to 1 wt. %, in each case based on the total amount of the cosmetic or pharmaceutical product.

Most preferred is a cosmetic composition comprising a combination of resorcinol derivatives of formula (I), respectively (II), preferably 4-butyl resorcinol, 4-hexyl resorcinol or phenylethyl resorcinol, and most preferred phenylethyl resorcinol (SymWhite 377®) with at least a further compound (b1), (b2) or (b3) which are preferably selected from ginger root CO2 extract, carnosine, L-carnosine, D-carnosine, D/L-carnosine, carcinine, carcinine*HCl (INCI: decarboxy carnosine*HCl), anserine, D-anserine, L-anserine, as well as L-anserine*HNO3, sclareolide, larixol. Preferably two, three or more of the aforementioned compounds are present in a cosmetic composition of the present invention.

Cosmetic and Pharmaceutical Preparations

Cosmetic and pharmaceutical preparations (medicaments) according to the present invention may include similar additives, such as for example oil bodies or emulsifiers. Therefore, the border between cosmetic and pharmaceutical preparations is in flow and it should be understood that components cited for one application are recommended for the other mutatis-mutandis without literal repetition.

The cosmetic and medicaments according may comprise typical auxiliaries and further additives as described aforementioned. Typical auxiliaries and further additives are such as mild surfactants, oil components, emulsifiers, pearlizing waxes, consistency-imparting agents, thickeners, superfatting agents, stabilizers, polymers, silicone compounds, fats, waxes, lecithins, phospholipids, moisturizers, biogenic agents, antioxidants, film-forming agents, expanding agents, insect repellents, self-tanning agents, tyrosine inhibitors (depigmenting agents), hydrotropes, solubilizers, preservatives, perfume oils, dyes and the like.

Surfactants

Examples of suitable surface-active substances that may be included are anionic, nonionic, cationic and/or amphoteric or zwitterionic surfactants, ordinarily contained in the agents in amounts of approx. 1 to 70, preferably 5 to 50, and particularly 10 to 30 wt %. Typical examples of anionic surfactants include soaps, alkylbenzene sulfonates, alkane sulfonates, olefin sulfonates, alkyl ether sulfonates, glycerol ether sulfonates, α-methyl ester sulfonates, sulfofatty acids, alkyl sulfates, alkylether sulfates, glycerol ether sulfates, fatty acid ether sulfates, hydroxy mixed ether sulfates, monoglyceride (ether) sulfates, fatty acid amide (ether) sulfates, mono- and dialkylsulfosuccinates, mono- and dialkylsulfosuccinamates, sulfotriglycerides, amide soaps, ether carboxylic acids and salts thereof, fatty acid isethionates, fatty acid sarcosinates, fatty acid taurides, N-acylamino acids such as acyl lactylates, acyl tartrates, acyl glutamates, and acyl aspartates, alkyl oligoglycoside sulfates, protein fatty acid condensates (particularly wheat-based vegetable products) and alkyl(ether)phosphates. If the anionic surfactants contain polyglycol ether chains, they may show a conventional homolog distribution, but preferably a narrow-range homolog distribution. Typical examples of nonionic surfactants are fatty alcohol polyglycol ethers, alkyl phenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucuronic acid derivatives, fatty acid N-alkyl glucamides, protein hydrolysates (particularly wheat-based vegetable products), polyol fatty acid esters, sugar esters, sorbitan esters, polysorbates, and amine oxides. If the nonionic surfactants contain polyglycol ether chains, they may show a conventional homolog distribution, but preferably a narrow-range homolog distribution. Typical examples of cationic surfactants are quaternary ammonium compounds such as dimethyl distearyl ammonium chloride, and esterquats, particularly quaternized fatty acid trialkanolamine ester salts. Typical examples of amphoteric or zwitterionic surfactants are alkylbetaines, alkylamidobetaines, aminopropionates, aminoglycinates, imidazolinium betaines, and sulfobetaines. The above-mentioned surfactants are exclusively known compounds. Typical examples of particularly suitable mild surfactants, i.e. those particularly well-tolerated by the skin, are fatty alcohol polylycolether sulfates, monoglyceride sulfates, mono- and/or dialkylsulfosuccinates, fatty acid isethionates, fatty acid sarcosinates, fatty acid taurides, fatty acid glutamates, α-olefin sulfonates, ether carboxylic acids, alkyl oligoglycosides, fatty acid glucamides, alkyl amidobetaines, and amphoacetal and/or protein fatty acid condensates, with the latter preferably being based on wheat proteins.

Oil Components

Suitable oil components are, for example, Guerbet alcohols based on fatty alcohols containing 6 to 18, and preferably 8 to 10 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$ fatty acids with branched alcohols, particularly 2-ethyl hexanol, esters of $C_{18}$-$C_{38}$-alkyl hydroxycarboxylic acids with linear or branched $C_6$-$C_{22}$ fatty alcohols, particularly dioctyl malate, esters of linear and/or branched fatty acids with polyhydric alcohols (such as propylene glycol, dimer diol, or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, particularly benzoic acid, esters of $C_2$-$C_{12}$ dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates such as dicaprylyl carbonate (Cetiol® CC), Guerbet carbonates based on fatty alcohols containing 6 to 18, and preferably 8 to 10 carbon atoms, esters of benzoic acid with linear and/or branched $C_6$-$C_{22}$-alcohols (such as Finsolv® TN), linear or branched, symmetrical or asymmetrical dialkyl ethers containing 6 to 22 carbon atoms per alkyl group, such as dicaprylyl ether (Cetiol® OE), ring-opening products of epoxidized fatty acid esters with polyols, silicone oils (cyclomethicone, silicon methicones, etc.) and/or aliphatic or naphthenic hydrocarbons such as squalane, squalene, or dialkyl cyclohexane.

Emulsifiers

Examples of suitable emulsifiers include nonionic surfactants from at least one of the following groups:
- addition products of 2 to 30 mol of ethylene oxide and/or 0 to 5 mol of propylene oxide to linear fatty alcohols with 8 to 22 carbon atoms, to fatty acids with 12 to 22 carbon atoms, to alkyl phenols with 8 to 15 carbon atoms in the alkyl group, as well as alkylamines with 8 to 22 carbon atoms in the alkyl residue;
- alkyl and/or alkenyl oligoglycosides with 8 to 22 carbon atoms the alk(en)yl residue and ethoxylated analogs thereof;
- addition products of 1 to 15 mol of ethylene oxide to castor oil and/or hardened castor oil;
- addition products of 15 to 60 mol of ethylene oxide to castor oil and/or hardened castor oil;
- partial esters of glycerol and/or sorbitan with unsaturated, linear or saturated, branched fatty acids with 12 to 22 carbon atoms and/or hydroxycarboxylic acids with 3 to 18 carbon atoms, as well as adducts thereof with 1 to 30 mol of ethylene oxide;
- partial esters of polyglycerol (average degree of self-condensation 2 to 8), polyethylene glycol (molecular weight 400 to 5000), trimethylolpropane, pentaerythrite, sugar alcohols (such as sorbite), alkyl glycosides (such as methyl glycoside, butyl glycoside, lauryl glycoside), as well as polyglycosides (such as cellulose) with saturated and/or unsaturated, linear or branched fatty acids with 12 to 22 carbon atoms and/or hydroxycarboxylic acids with 3 to 18 carbon atoms, as well as adducts thereof with 1 to 30 mol of ethylene oxide;
- mixed esters of pentaerythrite, fatty acids, citric acid and fatty alcohols and/or mixed esters of fatty acids containing 6 to 22 carbon atoms, methyl glucose and polyols, preferably glycerol or polyglycerol.
- mono, di- and trialkylphosphates, as well as mono, di- and/or tri-PEG-alkyl phosphates and salts thereof;

wool wax alcohols;
polysiloxane/polyalkyl/polyether copolymers or corresponding derivatives;
block copolymers such as polyethylene glycol-30 dipolyhydroxystearate;
polymer emulsifiers, such as Pemulen polymers (TR-1, TR-2) from Goodrich or Cosmedia® SP from Cognis;
polyalkylene glycols, and
glycerol carbonates.

In the following, particularly suitable emulsifiers are described in further detail:

Alkoxylates. The addition products of ethylene oxide and/or propylene oxide to fatty alcohols, fatty acids, alkyl phenols, or castor oil constitute known, commercially available products. These are homolog mixtures whose average degree of alkoxylation corresponds to the ratio of the amounts of ethylene oxide and/or propylene oxide to the substrates with the addition reaction was carried out. $C_{12/18}$-fatty acid mono and diesters of addition products of ethylene oxide to glycerol are known as refatting agents for cosmetic preparations.

Alkyl and/or alkenyl oligoglycosides. Alkyl and/or alkenyl oligoglycosides and the production and use thereof are known from prior art. In particular they are produced by reacting glucose or oligosaccharides with primary alcohols having 8 to 18 carbon atoms. With the respect to the glycoside residue, both monoglycosides, in which a cyclic sugar residue is glycosidically bonded to the fatty alcohol, and oligomeric glycosides, preferably having a degree of oligomerization of approx. 8, are suitable. In this case, the degree of oligomerization is an average statistical value based on the usual homolog distribution for such technical products.

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride, and technical mixtures thereof that can secondarily contain small amounts of triglycerides from the production process. Addition products of 1 to 30, and preferably 5 to 10 mol of ethylene oxide to the above-mentioned partial glycerides are also suitable.

Sorbitan esters. Examples of suitable sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical mixtures thereof. Addition products of 1 to 30 and preferably 5 to 10 mol of ethylene oxide to the above-mentioned sorbitan esters are also suitable.

Polyglycerol esters. Typical examples of suitable polyglycerol esters are polyglyceryl-2 dipolyhydroxystearate (Dehymuls® PGPH), polyglyceryl-3-diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32), polyglyceryl polyricinoleate (Admul® WOL 1403), polyglyceryl dimerate isostearate, and mixtures thereof. Examples of further suitable polyol esters are mono, di, and triesters, optionally reacted with 1 to 30 mol of ethylene oxide, of trimethylol propane or pentaerythrite with lauric acid, coconut fatty acid, tallow fatty acid, palmitic acid, stearic acid, oleic acid, behenic acid and the like.

Anionic emulsifiers. Typical anionic emulsifiers are aliphatic fatty acids with 12 to 22 carbon atoms, such as palmitic acid, stearic acid or behenic acid, as well as dicarboxylic acids with 12 to 22 carbon atoms, such as azelaic acid or sebacic acid.

Amphoteric and cationic emulsifiers. Zwitterionic surfactants can also be used as emulsifiers. Zwitterionic surfactants are surface-active compounds that carry at least one quaternary ammonium group and at least one carboxylate and a sulfonate group in the molecule. Particularly suitable zwitterionic surfactants are the so-called betaines, including N-alkyl-N,N-dimethylammonium glycinates such as coconut alkyl dimethylammonium glycinate, N-acylaminopropyl-N,N-dimethylammonium glycinates such as coconut acyl-aminopropyldimethyl ammoniumglycinate, and 2-alkyl-3-carboxylmethyl-3-hydroxyethylimidazolines containing 8 to 18 carbon atoms in their alkyl or acyl groups, as well as coconut acylaminoethyl hydroxyethyl carboxymethyl glycinate. Particularly preferred is the fatty acid amide derivative known under the CTFA name cocamidopropyl betaine. Ampholytic surfactants are also suitable emulsifiers. Ampholytic surfactants are surface-active compounds that, in addition to a $C_{8/18}$ alkyl or acyl group, contain at least one free amino group and at least one —COOH— or —SO$_3$H group in the molecule and are capable of forming inner salts. Examples of suitable ampholytic surfactants include N-alkyl glycines, N-alkyl propionic acids, N-alkyl aminobutyric acids, N-alkyl iminodipropionic acids, N-hydroxyethyl-N-alkyl amidopropylglycine, N-alkyl taurine, N-alkyl sarcosine, 2-alkyl amino-propionic acids and alkyl aminoacetic acids with approx. 8 to 18 carbon atoms in their alkyl groups. Particularly preferred ampholytic surfactants are N-coconut alkyl aminopropionate, coconut acyl aminoethylaminopropionate, and $C_{12/18}$ acyl sarcosine. Finally, cationic surfactants are also suitable as emulsifiers, with those of the esterquat type, preferably methyl quaternized difatty acid triethanolamine ester salts, being particularly preferred.

Fats and Waxes

Typical examples of fats are glycerides, i.e. solid or liquid vegetable or animal products consisting essentially of mixed glycerol esters of higher fatty acids; examples of suitable waxes include natural waxes, such as candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygial fat, ceresin, ozocerite (earth wax), petrolatum, paraffin waxes, and microwaxes; chemically modified waxes (hard waxes), such as montan ester waxes, sasol waxes, hydrogenated jojoba waxes, as well as synthetic waxes such as polyalkylene waxes and polyethylene glycol waxes. In addition to the fats, fatlike substances such as lecithins and phospholipids are also suitable as additives. The person skilled in the art understands the term lecithins to refer to glycero-phospholipids formed from fatty acids, glycerol, phosphoric acid, and choline by esterification. Lecithins are therefore frequently referred to by specialists as phosphatidyl cholines (PC). Examples of suitable natural lecithins include the kephalins, also referred to as phosphatidic acids, and which are derivatives of 1,2-diacyl-sn-glycerol-3-phosphoric acids. In contrast, phospholipids are ordinarily understood to be mono- and preferably diesters of phosphoric acid with glycerol (glycerol phosphates) that are generally classified as fats. In addition, sphingosines or sphingolipids are also suitable.

Examples of suitable pearlizing waxes include alkylene glycol esters, particularly ethylene glycol distearate; fatty acid alkanolamides, particularly coconut fatty acid diethanolamide; partial glycerides, particularly stearic acid monoglyceride; esters of polyvalent, optionally hydroxy-substituted carboxylic acids with fatty alcohols containing 6 to 22 carbon atoms, particularly long-chain esters of tartaric acid; fatty substances such as fatty alcohols, fatty ketones, fatty aldehydes, fatty ethers, and fatty carbonates that have a total of at least 24 carbon atoms, particularly laurone and distearyl ether; fatty acids such as stearic acid, hydroxystearic acid, or behenic acid, ring opening products of olefin epoxides having 12 to 22 carbon atoms with fatty alcohols having 12 to 22 carbon atoms and/or polyols having 2 to 15 carbon atoms and 2 to 10 hydroxyl groups, as well as mixtures thereof.

Coolants

Coolants are compounds that produce a feeling of coolness on the skin. As a rule, these are menthol compounds, which—in addition to the base component menthol itself-contain substances selected from the group comprising menthol methyl ether, menthone glyceryl acetal (FEMA GRAS 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomenthyl glutamate (FEMA GRAS 4006), menthoxy-1,2-propane diol (FEMA GRAS 3784), menthoxy-2-methyl-1,2-propane diol (FEMA GRAS 3849), and the methane carboxylic acid esters and amides WS-3, WS-4, WS-5, WS-12, WS-14, and WS-30, as well as mixtures thereof.

A first important representative of these substances is monomenthyl succinate (FEMA GRAS 3810). Both the succinate and the analogous monomenthyl glutarate (FEMA GRAS 4006) constitute important representatives of monomenthyl esters based on di- and polycarboxylic acids:

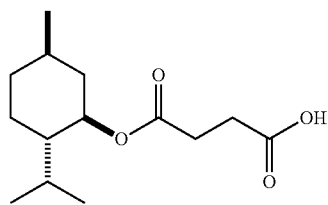

-continued

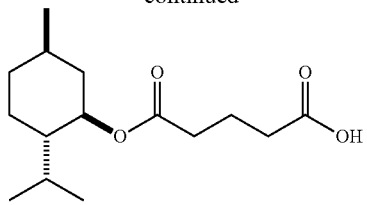

Examples of uses of these substances can be found for example in the documents WO 2003 043431 (Unilever) or EP 1332772 A1 (IFF).

The next important group of preferred menthol compounds within the meaning of the invention comprises carbonate esters of menthol and polyols, including glycols, glycerol, or carbohydrates, such as menthol ethylene glycol carbonate (FEMA GRAS 3805=Frescolat® MGC), menthol propylene glycol carbonate (FEMA GRAS 3784=Frescolat® MPC), menthol 2-methyl-1,2-propane diol carbonate (FEMA GRAS 3849) or the corresponding sugar derivatives. Also preferred are the menthol compounds menthyl lactate (FEMA GRAS 3748=Frescolat® ML), and particularly menthone glyceryl acetal (FEMA GRAS 3807) or menthone glyceryl ketal (FEMA GRAS 3808), which is marketed under the name Frescolat® MGA, menthyl ethylamide oxalate, which is marketed under the name Frescolat® X-Cool. Among these substances, menthone glyceryl acetal/ketal, menthyl lactate, menthol ethylene glycol carbonate, menthyl ethylamide oxalate or menthol propylene glycol carbonate have been found to be particularly advantageous, and are marketed by the Applicant under the names Frescolat® MGA, Frescolat® ML, Frescolat® MGC, Frescolat® X-cool and Frescolat® MPC.

Menthol compounds having a C—C bond at position 3 and from which a series of representatives can also be used was first developed in the 1970s. These substances are generally referred to as WS types. The base component is a menthol derivative in which the hydroxyl group has been replaced with a carboxyl group (WS-1). All other types of WS, such as the preferred species WS-3, WS-4, WS-5, WS-12, WS-14 and WS-30, are derived from this structure.

Consistency-Imparting Agents and Thickeners

Suitable consistency-imparting agents are primarily fatty alcohols or hydroxy fatty alcohols with 12 to 22, and preferably 16 to 18 carbon atoms, as well as partial glycerides, fatty acids, or hydroxy fatty acids. A combination of these substances with alkyl oligoglycosides and/or fatty acid-N-methylglucamides of the same chain length and/or polyglyceryl poly-12-hydroxystearates is preferred. Examples of suitable thickeners are aerosil types (hydrophilic silicic acids), polysaccharides, particularly xanthan gum, guar-guar, agar-agar, alginates and tyloses, carboxymethylcellulose and hydroxyethyl- and hydroxypropylcellulose, as well as higher-molecular polyethylene glycol mono- and diesters of fatty acids, polyacrylates (such as Carbopole® and Pemulen products from Goodrich; Synthalene® from Sigma; Keltrol products from Kelco; Sepigel products from Seppic; Salcare products from Allied Colloids) polyacrylamides, polymers, polyvinyl alcohol, and polyvinyl pyrrolidone. Bentonites such as Bentone® Gel VS-5PC (Rheox) have also been found to be particularly effective, comprising a mixture of cyclopentasiloxane, disteardimonium hectorite, and propylene carbonate. Also suitable are surfactants such as ethoxylated fatty acid glycerides, esters of fatty acids with polyols such as pentaerythrite or trimethylol propane, fatty alcohol ethoxylates having narrow-range homolog distribution, or alkyl oligoglycosides, as well as electrolytes such as table salt and ammonium chloride.

Superfatting Agents and Stabilizers

Examples of suitable superfatting agents are substances such as lanolin and lecithin, as well as polyethoxylated or acylated lanolin and lecithin derivatives, polyol fatty acid esters, monoglycerides, and fatty acid alkanolamides, wherein the latter simultaneously serve as foam stabilizers.

Metal salts of fatty acids, such as magnesium, aluminum and/or zinc stearate or ricinoleate, can be used as stabilizers.

Polymers

Examples of suitable cationic polymers include cationic cellulose derivatives such as a quaternized hydroxyethylcellulose available under the name Polymer JR 400® from Amerchol, cationic starch, copolymers of diallyl ammonium salts and acrylamides, quaternized vinyl pyrrolidone/vinyl imidazole polymers such as Luviquat® (BASF), condensation products of polyglycols and amines, quaternized collagen polypeptides such as lauryldimonium hydroxypropyl hydrolyzed collagen (Lamequat®L/Grinau), quaternized wheat polypeptides, polyethylene imine, cationic silicone polymers such as amodimethicone, copolymers of adipic acid and dimethylaminohydroxypropyldiethylene triamine (Cartaretine®/Sandoz), copolymers of acryl acid with dimethyl diallyl ammonium chloride (Merquat® 550/Chemviron), polyaminopolyamides and crosslinked water-soluble polymers thereof, cationic chitin derivatives such as quaternized chitosan, optionally distributed in microcrystalline form, condensation products of dihalogen alkylene such as dibromobutane with bis-dialkylamines such as bis-dimethylamino-1,3-propane, cationic guar-gums such as Jaguar® CBS, Jaguar® C-17, and Jaguar® C-16 from Celanese, and quaternized ammonium salt polymers such as Mirapol® A-15, Mirapol® AD-1, and Mirapol® AZ-1 from Miranol.

Examples of suitable anionic, zwitterionic, amphoteric, and nonionic polymers include vinyl acetate/crotonic acid copolymers, vinyl pyrrolidone/vinyl acrylate copolymers, vinyl acetate/butyl maleate/isobornyl acrylate copolymers, methylvinyl ether/maleic acid anhydride copolymers and esters thereof, non-crosslinked polyacrylic acids and polyacrylic acids crosslinked with polyols, acrylamidopropyl trimethylammonium chloride/acrylate copolymers, octylacrylamide/methyl methacrylate/tert-butyl aminoethyl methacrylate/2-hydroxypropyl methacrylate copolymers, polyvinyl pyrrolidone, vinyl pyrrolidone/vinyl ace-tate copolymers, vinyl pyrrolidone/dimethylaminoethyl methacrylate/vinyl caprolactam terpolymers, and optionally, derivatized cellulose ethers and silicones.

Silicone Compounds

Suitable silicone compounds are for example dimethyl polysiloxane, methylphenyl polysiloxane, cyclic silicones, as well as amino, fatty acid, alcohol, polyether, epoxy, fluorine, glycoside, and/or alkyl-modified silicone compounds, which can be present at room temperature either in liquid or resinous form. Also suitable are simethicones, which are mixtures of dimethicones having an average chain length of 200 to 300 dimethylsiloxane units and hydrogenated silicates.

Moisturizers

Moisturizers are used for further optimization of the sensory properties of the composition and for moisture regulation of the skin. At the same time, the cold stability of the preparations according to the invention is increased, particularly in the case of emulsions. The moisturizers are ordinarily contained in an amount of 0.1 to 15 wt %, preferably 1 to 10 wt %, and particularly preferably 5 to 10 wt %.

Examples of suitable moisturizers according to the invention include amino acids, pyrrolidone carboxylic acid, lactic acid and salts thereof, lactitol, urea and urea derivatives, uric acid, glucosamine, creatinine, cleavage products of collagen, chitosan or chitosan salt derivatives, and particularly polyols and polyol derivatives (such as glycerol, diglycerol, triglycerol, ethylene glycol, propylene glycol, butylene glycol, erythrite, 1,2,6-hexane triol, polyethylene glycols such as PEG-4, PEG-6, PEG-7, PEG-8, PEG-9, PEG-10, PEG-12, PEG-14, PEG-16, PEG-18, and PEG-20), sugar and sugar derivatives (including fructose, glucose, maltose, maltitol, mannite, inosite, sorbite, sorbityl silane diol, sucrose, trehalose, xylose, xylite, glucuronic acid and salts thereof), ethoxylated sorbite (sorbeth-6, sorbeth-20, sorbeth-30, sorbeth-40), honey and hardened honey, hardened starch hydrolysates, as well as mixtures of hardened wheat protein and PEG-20/acetate copolymer. Preferred suitable moisturizers according to the invention are glycerol, diglycerol, triglycerol, and butylene glycol.

Biogenic Active Ingredients and Antioxidants

Biogenic active ingredients are understood to be e.g. tocopherol, tocopherol acetate, tocopherol palmitate, ascorbic acid, (deoxy)ribonucleic acid and fragmentation products thereof, β-glucan, retinol, bisabolol, allantoin, phytantriol, panthenol, AHA acids, amino acids, ceramides, pseudoceramides, essential oils, and plant extracts such as *Zingiber Officinale* (Ginger) Root Extract, *Echinacea Purpurea* Extract, prune extract, bambara extract, vitamin complexes, and benzylidene dimethoxydimethylindanone Antioxidants interrupt the photochemical reaction chain triggered when UV radiation penetrates the skin. Typical examples of these are amino acids (such as glycine, histidine, tyrosine, tryptophan) and derivatives thereof, imidazoles (such as urocanic acid) and derivatives thereof, carotenoids, carotenes (such as α-carotene, β-carotene, lycopene) and derivatives thereof, chlorogenic acid and derivatives thereof, liponic acid and derivatives thereof (such as dihydroliponic acid), aurothioglucose, propylthiouracil and other thiols (such as thioredoxin, glutathione, cysteine, cystine, cystamine and glycosyls thereof, N-acetyl, methyl, ethyl, propyl, amyl, butyl and lauryl, palmitoyl, oleyl, γ-linoleyl, cholesteryl and glyceryl esters), as well as salts thereof, dilauryl thiodipropionate, distearyl thiodipropionate, thiodipropionic acid and derivatives thereof (esters, ethers, peptides, lipids, nucleotides, nucleosides and salts), as well as sulfoximine compounds (such as buthionine sulfoximine, homocysteine sulfoximine, buthionine sulfone, penta, hexa, heptathionine sulfoximine) in very low tolerated doses (such as pmol to pmol/kg), as well as (metal) chelators (such as α-hydroxy fatty acids, palmitic acid, phytic acid, and lactoferrin), α-hydroxy acids (such as citric acid, lactic acid, and malic acid), humic acid, gallic acid, gall extracts, bilirubin, biliverdin, EDTA, EGTA and derivatives thereof, unsaturated fatty acids and derivatives thereof (such as γ-linolenic acid, linoleic acid, and oleic acid), folic acid and derivatives thereof, ubiquinone, ubiquinol and derivatives thereof, Vitamin C and derivatives thereof (such as ascorbyl palmitate, Mg ascorbyl phosphate, ascorbyl acetate), tocopherols and derivatives thereof (such as Vitamin E acetate), Vitamin A and derivatives thereof (vitamin A palmitate), as well as coniferyl benzoate of benzoin, rutic acid and derivatives thereof, α-glycosylrutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (such as ZnO, ZnSO$_4$), selenium and derivatives thereof (such as selenium methionine), stilbene and derivatives thereof (such as stilbene oxide, trans-stilbene oxide), and suitable derivatives of the above-mentioned active ingredients according to the invention (salts, esters, ethers, sugars, nucleotides, nucleosides, peptides, and lipids).

Film-Forming Agents, Antidandruff Agents, and Expanding Agents

Examples of common film-forming agents include chitosan, microcrystalline chitosan, quaternized chitosan, polyvinyl pyrrolidone, vinyl pyrrolidone-vinyl acetate copolymerisates, polymers of the acrylic acid series, quaternary cellulose derivatives, collagen, hyaluronic acid or salts thereof, and similar compounds.

Examples of suitable antidandruff active ingredients include piroctone olamine (1-hydroxy-4-methyl-6-(2,4,4-trimethylpentyl)-2-(1H)-pyridinone monoethanolamine salt), Baypival® (climbazole), Ketoconazol®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, Elubiol, selenium disulfide, colloidal sulfur, sulfur polyethylene glycol sorbitan monooleate, sulfur rizinol polyethoxylate, sulfur-tar distillates, salicylic acid (or in combination with hexachlorophene), undecylenic acid monoethanolamide sulfosuccinate Na salt, Lamepon® UD (protein-undecylenic acid condensate), zinc pyrithione, aluminum pyrithione, and magnesium pyrithione/dipyrithione magnesium sulfate.

Examples of suitable expanding agents for aqueous phases are montmorillonite, clay mineral substances, Pemulen, as well as alkyl-modified carbopol products (Goodrich). Further suitable polymers or expanding agents can be seen in the overview of R. Lochhead in Cosm. Toil. 108, 95 (1993).

Insect Repellents

Examples of suitable insect repellents include N,N-diethyl-m-toluamide, 1,2-pentane diol, or ethyl butyl acetyl aminopropionates. Suitable self-tanning agents include dihydroxyacetone. Examples of suitable tyrosine inhibitors, which prevent the formation of melanin and are used in depigmentation agents, include arbutin, ferulic acid, kojic acid, cumaric acid, and ascorbic acid (Vitamin C).

Hydrotropes

Moreover, hydrotropes, such as ethanol, isopropyl alcohol, or polyols can be used in order to improve flow properties; these substances largely correspond to the carriers described at the outset. In this case, suitable polyols preferably have 2 to 15 carbon atoms, and at least two hydroxyl groups. The polyols can also include other functional groups, particularly amino groups, or be modified with nitrogen. Typical examples are
  glycerol;
  alkylene glycols, such as ethylene glycol, diethylene glycol, propylene glycol, butylene glycol, hexylene glycol, as well as polyethylene glycols with an average molecular weight of 100 to 1,000 daltons;
  technical oligoglycerol mixtures having a degree of self-condensation of 1.5 to 10 such as technical diglycerol mixtures with a diglycerol content of 40 to 50 wt %;
  methylol compounds, particularly trimethylol ethane, trimethylol propane, trimethylol butane, pentaerythrite, and dipentaerythrite;
  lower alkyl glycosides, particularly those with 1 to 8 carbon atoms in the alkyl residue, such as methyl and butyl glycoside;
  sugar alcohols with 5 to 12 carbon atoms, such as sorbite or mannite,
  sugars with 5 to 12 carbon atoms, such as glucose or saccharose;
  amino sugars, such as glucamine;
  dialcoholamines, such as diethanolamine or 2-amino-1,3-propane diol.

Preservatives

Examples of suitable preservatives include phenoxyethanol, formaldehyde solution, parabens, pentane diol, or sorbic acid, as well as the silver complexes known under the name Surfacine® and the additional substance classes listed in Appendix 6, sections A and B of the Cosmetics Ordinance.

Preference is made to preservatives which are selected from the group consisting of o-cymen-5-ol, benzoic acid and para-hydroxybenzoic acid, their esters and salts, Benzyl benzoate, propionic acid and its salts, salicylic acid and its salts, 2,4-hexadienoic acid (sorbic acid) and its salts, levulinic acid and its salts, anisic acid and its salts, perillic acid and its salts, cinnamic acid and its salts, formaldehyde and paraformaldehyde, 4-hydroxy benzaldehyde, ortho-, meta-, and para-anisic aldehyde, cinnamic aldehyde, cinnamic alcohol, 2-hydroxybiphenyl ether and its salts, 2-zinc-sulfidopyridine N-oxide, inorganic sulfites and bisulfites, sodium iodate, chlorobutanolum, 4-ethylmercury-(II)5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexame-thylenediguanide) hydrochloride, (Benzyloxymethoxy)-methanol hexamethylenetetramine, 1-(3-chloroallyl)-3,5,7-triaza-1-azonia-adamantane chloride, 1-(4-chlorophenoxy)-1-(1H-imidazol-1-yl)-3,3-dimethyl-2-butanone, 1,3-bis-(hydroxyme-thyl)-5,5-dimethyl-2,4-imidazolidinedione, 1,2-dibromo-2,4-dicyanobutane, 2,2'-methylene-bis(6-bromo-4-chlorophenol), bromochlorophene, mixture of 5-chloro-2-methyl-3(2H)-isothiazolinone, 2-methyl-3(2H)-isothiazolinone and with magnesium chloride and magnesium nitrate, 2-Octyl-2H-isothiazol-3-one, 1,2-benzisothiazol-3(2H)-one, 2-benzyl-4-chlorophenol, 3-(4-Chlorphenoxy)-1,2-propanediol (Chlorphenesin), 2-chloroacetamide, chlorhexidine, chlorhexidine acetate, chlorhexidine gluconate, chlorhexidine hydrochloride, N-alkyl(C12-C22)trimethyl-ammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidino-phenoxy)-n-hexane and its salts, glutaraldehyde, 5-ethyl-1-aza-3,7-dioxabicyclo(3.3.0) octane, 3-(4-chlorophenoxy)-1,2-propanediol, hyamines, alkyl-(C8-C18)-dimethyl-benzyl-ammonium chloride, alkyl-(C8-C18)-dimethyl-benzylammonium bromide, alkyl-(C8-C18)-dimethyl-benzyl-ammonium saccharinate, benzyl hemiformal, 3-iodo-2-propynyl butylcarbamate, sodium hydroxymethyl-aminoacetate or sodium hydroxymethyl-aminoacetate, imidazolidinylurea, diazolidinylurea, sodium hydroxymethylglycinate, DMDM hydantoin, Tropolone, (Ethylendioxy)dimethanol, 2-Brom-2-(brommethyl)pentandinitril, N-(3-Aminopropyl)-N-dodecylpropan-1,3-diamin, α,α',α''-trimethyl-1,3,5-triazine-1,3,5(2H,4H,6H)-triethanol, pyridine-2-thiol-1-oxide, sodium salt, Tetrahydro-1,3,4, 6-tetrakis(hydroxymethyl)imidazo[4,5-d]imidazol-2,5(1H, 3H)-dion, 1,3-bis(hydroxymethyl)-1-(1,3,4-tris (hydroxymethyl)-2,5-dioxoimidazolidin-4-yl)urea (Diazolidinyl Urea), 1,3-Bis(hydroxymethyl)-5,5-dimethylimidazolidine-2,4-dione, 3-Acetyl-2-hydroxy-6-methyl-4H-pyran-4-one, cetyl pyridium chloride, ethyl-N-alpha-dodecanoyl-L-arginate hydrochloride, caprylhydroxamic acid, sorbohydroxamic acid, and their mixtures.

Multifunctionals

The cosmetic or pharmaceutical preparations of the present invention particularly contain at least one compound of formula (I) or a cosmetically acceptable salt of a compound of formula (I) or a mixture containing two or more of these compounds or the salts thereof in combination with so called multifunctionals which are selected from the group consisting of 1,3-propanediol, methyl propanediol, 1,2-pentanediol, 1,2-hexanediol, 1,2-octanediol, 1,2-decanediol, 1,5-pentanediol, 1,6-hexanediol, 1,8-octanediol, 1,2-decanediol, ethylhexylglycerin, hexoxy-propan-1,2-diol, heptoxy-propan-1,2-diol, octoxy-propan-1,2-diol, 3-phenoxy-propan-1,2-diol, 3-benzyloxy-propan-1,2-diol, 3-phenylethyloxy-propan-1,2-diol, 3-phenylpropyloxy-propan-1,2-diol, 3-methylbenzyloxy-propan-1,2-diol, sorbitan caprylate, triclosan, climbazole, Octopirox (1-hydroxy-4-methyl-6-(2,4,4-trimethylpentyl)-2(1H)-pyridone, 2-aminoethanol), chitosan, farnesol, 2-butyloctanoic acid, 2-Benzylheptan-1-ol, glycerol monolaurate, bis(2-pyridylthio)zinc 1,1'-dioxide, N,N'-(decane-1,10-diyldipyridin-1-yl-4-ylidene)-dioctan-1-amine dihydrochloride (octenidine dihydrochloride), thymol, eugenol, 4-isopropyl-3-methylphenol, benzyl alcohol, 2-phenyethyl alcohol, 3-phenyl propanol, 2-phenoxyethanol, 1-phenoxy-propan-2-ol, 3-phenoxypropanol, benzyloxymethanol, glyceryl caprylate, glyceryl caprate, glyceryl laurate, hydroxy-acetophenone, and mixtures thereof.

The preferred cosmetic or pharmaceutical preparation of the present invention, preferably comprises a combination of resorcinol derivatives of formula (I), respectively (II), preferably 4-butyl resorcinol, 4-hexyl resorcinol or phenylethyl resorcinol, and most preferred phenylethyl resorcinol (SymWhite 377®) with multifunctionals selected from 2-pentanediol, 1,2-hexanediol, 1,2-octanediol, 1,2-decanediol, hydroxyacetophenone, and mixtures thereof. The combination of the resorcinol derivative of formula (I), respectively (11), preferably 4-butyl resorcinol, 4-hexyl resorcinol or phenylethyl resorcinol, and most preferred phenylethyl resorcinol (SymWhite 377®) with the multifunctionals are especially advantageously for the treatment of sunlight preferably visible light induced hyperpigmentation.

Perfume Oils and Fragrances

Examples of suitable perfume oils include mixtures of natural and synthetic fragrances. Natural fragrances are flower extracts (lily, lavender, rose, jasmine, neroli, ylang-ylang), stems and leaves (geranium, patchouli, petitgrain), fruits (anise, coriander, caraway, juniper), fruit peels (bergamot, lemon, orange), roots (nutmeg, *angelica*, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*galbanum*, elemi, benzoin, myrrh, olibanum, opoponax). Animal raw materials such as civet and beaver may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert-butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propi-onate, styrallyl propionate and benzyl salicylate. Ethers include benzyl ethyl ether, while aldehydes include linear alkanals containing 8 to 18 carbon atoms, citral, citronellal, citronellyl oxyacetaldehyde, cyclamen aldehyde, hydroxycitronellal, lilial and bourgeonal; examples of suitable ketones are the ionones, α-isomethylionone, and methyl cedryl ketone. Suitable alcohols are anethol, citronellol, eugenol, isoeugenol, geraniol, linalool, phenylethyl alcohol, and terpineol. The hydrocarbons chiefly include the terpenes and balsams. However, mixtures of different perfume compounds are preferred that produce an agreeable fragrance together. Other suitable perfume oils include essential oils of low volatility that are mostly used as aroma components, such as sage oil, camomile oil, clove oil, melissa oil, mint oil, cinnamon leaf oil, lime-blossom oil, juniper berry oil, vetiver oil, olibanum oil, *galbanum* oil, *ladanum* oil, and lavendin oil. Preferably, bergamot oil, dihydromyrcenol, lilial, lyral, citronellol, phenylethyl alcohol, α-hexylcinnamaldehyde, geraniol, benzyl acetone, cyclamen aldehyde, linalool, boisambrene forte, ambroxan, indole, hedione, sandelice, citrus oil, mandarin oil, orange oil, allyl amyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillate, irotyl, and floramate are used either individually or in mixtures.

Examples of suitable fragrances include peppermint oil, spearmint oil, anise oil, star anise oil, caraway oil, *eucalyptus* oil, fennel oil, citrus oil, wintergreen oil, clove oil, menthol, and the like.

Dyes

The dyes that can be used are those suitable and approved for cosmetic purposes, such as those listed in the publication "Cosmetic Dyes" of the Farbstoffkommission der Deutschen Forschungsgemeinschaft [Dyes Commission of the German Research Foundation], Verlag Chemie, Weinheim, 1984, pp. 81-106. Examples are cochineal red A (C.I. 16255), patent blue V (C.I.42051), indigotin (C.I.73015), chlorophyllin (C.I.75810), quinoline yellow (C.I.47005), titanium dioxide (C.I.77891), indanthrene blue RS (C.I. 69800) and alizarin red (C.I.58000). Luminol can also be included as a luminescent dye. These dyes are ordinarily used in concentrations of 0.001 to 0.1 wt % relative to the entire mixture.

The total amount of these auxiliaries and additives can be 1 to 50, and preferably 5 to 40 wt % relative to the agent. The agent can be produced by common cold or hot processes; the phase inversion temperature mode is preferred.

INDUSTRIAL APPLICATION

An important aspect of the present invention refers to a non-therapeutical method for treating hyperpigmentation, in sunlight induced, preferably visible light induced hyperpigmentation, comprising the following steps:
(i) providing a preferred (pharmaceutical or cosmetic) composition as described aforementioned comprising a resorcinol derivative of formula (I), respectively (II), preferably 4-butyl resorcinol, 4-hexyl resorcinol or phenylethyl resorcinol, and most preferred phenylethyl resorcinol (SymWhite 377®), and
(ii) applying said composition to human skin.

Particularly, the method is preferably directed to ginger root $CO_2$ extract containing, consisting or essentially consisting of

| (a) | 25 to 30 | % b.w. [6]-gingerol |
| (b) | 5 to 10 | % b.w. [8]-gingerol |
| (c) | 5 to 10 | % b.w. [10]-gingerol |
| (d) | 1.5 to 4 | % b.w. [6]-shogaol |
| (e) | 0.3 to 1.3 | % b.w. [8]-shogaol; |
| (f) | 0.03 to 1 | % b.w. [10]-shogaol; |
| (g) | 0.01 to 1 | % b.w. zingerone, | on condition that the amount of gingerols sums up to 35 to 50% b.w. and the amount of shogaols sums up to 1.5 to 6% b.w.

Preference is made to the method in which the cosmetic/pharmaceutical preparation further comprises, consists or essentially consisting of at least one UV filters, wherein the UV filters are selected from the group consisting of UV-A filters, UV-B filters, and light protection pigments.

Also preferred is a method in which the cosmetic/pharmaceutical preparation further comprises consists or essentially consisting of at least one skin lightening agent. In a preferred embodiment the preparations are in the form of creams, lotions, gels, pastes or capsules representing skin care or sun protection compositions.

Preference is also made to a method, wherein resorcinol derivative of formula (I), respectively (II), preferably 4-butyl resorcinol, 4-hexyl resorcinol or phenylethyl resorcinol, and most preferred phenylethyl resorcinol (SymWhite 377®) is present in an active amount to reduce, retard, suppress and/or protect against sunlight induced, preferably visible light induced hyperpigmentation.

A further aspect of the present invention is another method of cosmetic, non-therapeutic treatment of a mammal, said method comprising effecting changes in mammalian skin pigmentation, preferably human skin, by administering to said mammal a pigmentation-changing effective amount of resorcinol derivative of formula (I), respectively (11), preferably 4-butyl resorcinol, 4-hexyl resorcinol or phenylethyl resorcinol, and most preferred phenylethyl resorcinol (SymWhite 377®).

Preferably the pigmentation-changing effective amount of the resorcinol derivative of formula (I), respectively (II), preferably 4-butyl resorcinol, 4-hexyl resorcinol or phenylethyl resorcinol, and most preferred phenylethyl resorcinol (SymWhite 377®) is administered topically.

Another further aspect of the present invention is a method of reducing, retarding and/or suppressing hyperpigmentation, respectively treating, preventing and/or ameliorating the formation of hyperpigmentation of skin which comprises topically applying a preferred (pharmaceutical or cosmetic) preparation as described aforementioned containing, consisting or essentially consisting of a resorcinol derivative of formula (I), respectively (II), preferably 4-butyl resorcinol, 4-hexyl resorcinol or phenylethyl resorcinol, and most preferred phenylethyl resorcinol (SymWhite 377®) and further additives to sunlight induced, preferably visible light induced hyperpigmented tissue of a human.

Optionally, further compounds (b1) from 0.05 wt. % to 60 wt. %, preferably 0.1 wt. % to 50 wt. %, and particularly preferably 0.5 wt. % to 40 wt. % of UV filters, and/or (b2) from 0.005 wt. % to 20 wt. %, preferably 0.01 wt. % to 10 wt. % of skin lightening agents, and/or (b3) from 0.0001 wt. % to 30 wt. %, preferably from 0.01 wt. % to 10 wt. % of antioxidants are present in the present preparations, wherein the weight percent of the compounds a) to d) are based on the total amount of the preparation and the sum of all compounds add to 100 wt. %, more preferably one of the compounds (b1), (b2) or (b3) is essentially contained in a preferred composition of the present invention. And in a further embodiment compounds (b1) and (b2) are essentially contained in a preferred composition of the present invention. In another embodiment compounds (b1) (b2) and (b3) are essentially contained in a preferred composition of the present invention.

Finally, the invention is directed to the use of resorcinol derivative of formula (I), respectively (II), preferably 4-butyl resorcinol, 4-hexyl resorcinol or phenylethyl resorcinol, and most preferred phenylethyl resorcinol (SymWhite 377®) for the treatment, prevention and/or amelioration of hyperpigmentation, particularly to reduce, retard, suppress and/or protect against sunlight induced, preferably visible light induced hyperpigmentation.

A further aspect of the present invention is the use of resorcinol derivative of formula (I), respectively (II), preferably 4-butyl resorcinol, 4-hexyl resorcinol or phenylethyl resorcinol, and most preferred phenylethyl resorcinol (SymWhite 377®) for reducing, retarding and/or suppressing hyperpigmentation, respectively treating, preventing and/or ameliorating the formation of hyperpigmentation of skin, in which a preferred (pharmaceutical or cosmetic) preparation as described aforementioned that comprises resorcinol derivative of formula (I), respectively (II), preferably 4-butyl resorcinol, 4-hexyl resorcinol or phenylethyl resorcinol, and most preferred phenylethyl resorcinol (SymWhite 377®) and further additives is topically applied to sunlight induced, preferably visible light induced hyperpigmented tissue of a human.

Further aspect is the non-therapeutical, cosmetically use of resorcinol derivatives of formula (I) respectively (II), preferably 4-butyl resorcinol, 4-hexyl resorcinol or phenylethyl resorcinol, and most preferred phenylethyl resorcinol (SymWhite 377®) for the treatment, prevention and/or amelioration of hyperpigmentation.

The aforementioned uses herein encompasses the preferred compositions and preparations comprising, consisting or essentially consisting of resorcinol derivative of formula (I), respectively (II), preferably 4-butyl resorcinol, 4-hexyl resorcinol or phenylethyl resorcinol, and most preferred phenylethyl resorcinol (SymWhite 377®).

EXAMPLES

Example 1

Human epidermal melanoma cells A375 were cultured in 6-well plates. The cells were exposed to visible light (480 J/cm2) with Hydrosun 750 equipped with KG1 filter. 48 h prior to and past to the irradiation the cells were treated with test compounds in non-cytotoxic concentrations. Melanocytes were lysed in a solution of NaOH. Melanin was quantified by measurement of absorbance at 405 nm and calculation based on a melanin standard curve.

TABLE 1

Visible light induced hyperpigmentation in vitro: inhibition vs. visible light induced

| Compound | Concentration [%] | Melanin [µg] | Inhibition [%] | Sign. |
|---|---|---|---|---|
| Untreated | | 0.4589 ± 0.0334 | | |
| Visible light irradiated | | 0.9731 ± 0.1024 | | ### |
| SymWhite ® 377 | 0.000068 | 0.5688 ± 0.0793 | 79 | ** |
| | 0.000210 | 0.5280 ± 0.0494 | 86 | *** |
| | 0.000680 | 0.4598 ± 0.1024 | 100 | *** |

TABLE 1-continued

Visible light induced hyperpigmentation in vitro: inhibition vs. visible light induced

| Compound | Concentration [%] | Melanin [µg] | Inhibition [%] | Sign. |
|---|---|---|---|---|
| Untreated | | 1.8632 ± 0.1932 | | |
| Visible light irradiated | | 2.9248 ± 0.1357 | | ### |
| 4-Hexylresorcinol | 0.000005 | 1.9616 ± 0.2899 | 91 | ** |
| | 0.000015 | 1.8407 ± 0.1988 | 102 | *** |
| | 0.000050 | 1.1668 ± 0.1312 | 166 | *** |
| Untreated | | 1.8632 ± 0.1932 | | |
| Visible light irradiated | | 2.9248 ± 0.1357 | | ### |
| 4-Butylresorcinol | 0.0000316 | 2.3136 ± 0.6518 | 58 | ** |
| | 0.0001000 | 1.8593 ± 0.5365 | 100 | *** |
| | 0.0003160 | 0.9849 ± 0.0738 | 183 | *** |

Significance:
$p < 0.001$ versus untreated;
* $P < 0.05$ versus visible light irradiated
** $P < 0.01$ versus visible light irradiated
*** $P < 0.001$ versus visible light irradiated It has been surprisingly shown that SymWhite® 377, 4-hexyl resorcinol and 4-butyl resorcinol significantly inhibit the visible light induced hyperpigmentation.

Example 2

The below formulations were applied on ex vivo human skin explants from abdominal surgery of a donor with phototype IV (Fitzpatrick scale). 48 h after the formulations were removed with a cotton pad. Skin explants were exposed to visible light (480 J/cm2) with Hydrosun 750 equipped with KG1 filter. Formulations were reapplied afterwards. 48 h later skin sections were prepared and melanin was stained by Fontana-Masson stain. Quantification of melanin was done by image analysis.

TABLE 3

Formulations applied to ex vivo human skin (all amounts w/w %)

| Phase | Ingredients | INCI | A | B | C |
|---|---|---|---|---|---|
| A. | H2O, demin. | Water (Aqua) | 84.75 | 84.55 | 84.70 |
| | Hydrolite-5 | Pentyleneglycol | 1.00 | 1.00 | 1.00 |
| B. | PCL liquid 100 | Cetearyl Octanoate | 3.00 | 3.00 | 3.00 |
| | Lanette O | Cetearyl Alcohol | 2.00 | 2.00 | 2.00 |
| | Mineral Oil 5° E | Mineral Oil | 3.00 | 3.00 | 3.00 |
| | Eutanol G PN | Octyldodecanol | 4.00 | 4.00 | 4.00 |
| | Abil 350 | Dimethicone | 0.50 | 0.50 | 0.50 |
| C. | Pemulen TR1 | Acrylates/C10-30 Alkyl Acrylate Crosspolymer | 0.20 | 0.20 | 0.20 |
| | Ultrez-21 | Acrylates/C10-30 Alkyl Acrylate Crosspolymer | 0.05 | 0.05 | 0.05 |
| D. | Sodium hydroxid Sol. 10% | Sodium Hydroxide | 0.50 | 0.50 | 0.50 |
| E. | SymWhite ® 377 | Phenylethyl Resorcinol | — | 0.50 | 0.20 |
| | Hydrolite-5 | Pentyleneglycol | 1.00 | 1.00 | 1.00 |
| | Sum | | 100.0 | 100.0 | 100.0 |

TABLE 4

Melanin formation after visible light irradiation on ex vivo human skin

| | % of melanin | Inhibition vs Placebo [%] |
|---|---|---|
| untreated | 33.22 ± 3.7 | |
| Placebo | 61.68 ± 1.7 | |
| 0.2% SymWhite ® 377 | 42.48 ± 2.6 | 67.5 |
| 0.5% SymWhite ® 377 | 25.91 ± 1.2 | 125.7 |

The following examples show formulations for various sun protection products that contain the preparations according to the invention. All amounts are to be understood as indicating wt %.

Cosmetic sun protection agent

| Components | Amount |
|---|---|
| Ethylhexyl cinnamic acid | 7.50 |
| Benzophenone-3 | 2.00 |
| Polyglyceryl dimer soyate | 0.80 |
| Sorbitan stearate | 1.00 |
| Tocopheryl acetate | 0.50 |
| Glyceryl stearate. PEG-100 Stearate | 3.00 |
| PEG-40. Hydrogenated castor oil | 1.00 |
| Titanium dioxide. Aluminum oxide hydrate. Dimethicone/methicone copolymer | 3.00 |
| Butyrospermum parkii (shea butter) | 1.00 |
| C12-15 alkyl benzoate | 6.50 |
| Butylene glycol | 5.00 |
| Xanthan gum | 0.30 |
| Disodium EDTA | 0.10 |
| Allantoin | 0.10 |
| Polyacrylamide. C13-14 isoparaffin. Laureth-7 | 1.00 |
| Pentylene glycol | 5.00 |
| 4-t-Butyl cyclohexanol | 1.00 |
| SymWhite ® 377 | 0.20 |
| Benzylidene Dimethoxydimethylindanone | 0.30 |
| Preservatives (methyl, butyl, ethyl, propylparaben, phenoxyethanol) | 0.30 |
| Aqua dem. | Ad 100 |

Sun protection spray (all amounts in wt. %)

| Components | INCI | A | B | C |
|---|---|---|---|---|
| Water, demineralized | Water (aqua) | 69.00 | 69.00 | 69.00 |
| Glycerol | Glycerol | 4.00 | 4.00 | 4.00 |
| 1,3-butylene glycol | Butylene glycol | 5.00 | 5.00 | 5.00 |
| D-Panthenol | Panthenol | 0.50 | 0.50 | 0.50 |
| Lara care A-200 | Galactoarabinan | 0.25 | 0.25 | 0.25 |
| Baysilone oil M 10 | Dimethicone | 1.00 | 1.00 | 1.00 |
| Edeta BD | Disodium EDTA | 0.10 | 0.10 | 0.10 |
| Copherol 1250 | Tocopheryl acetate | 0.50 | 0.50 | 0.50 |
| Cetiol OE | Dicaprylyl ether | 3.00 | 3.00 | 3.00 |
| Neo Heliopan ® HMS | Homosalate | 5.00 | 5.00 | 5.00 |
| Neo Heliopan ® AV | Ethylhexyl methoxycinnamate | 6.00 | 6.00 | 6.00 |
| Neo Heliopan ® 357 | Butyl methoxydibenzoyl methane | 1.00 | 1.00 | 1.00 |
| Corapan TQ | Diethylhexylnaphthalate | 2.00 | 2.00 | 2.00 |
| Alpha Bisabolol | Bisabolol | 0.10 | 0.10 | 0.10 |
| Pemulen TR-2 | Acrylates/C10-30 alkyl acrylate crosspolymer | 0.25 | 0.25 | 0.25 |
| NaOH 10% | Sodium hydroxide | 0.60 | 0.60 | 0.60 |
| Perfume oil | Fragrance | 0.20 | 0.20 | 0.20 |
| Phenoxyethanol | Phenoxyethanol | 0.40 | 0.40 | 0.40 |
| SymSave ® H | Hydroxyacetophenone | 0.50 | 0.50 | 0.50 |
| Solbrol M | Methylparaben | 0.10 | 0.10 | 0.10 |
| Solbrol P | Propylparaben | 0.10 | 0.10 | 0.10 |
| SymWhite ® 377 | Phenylethyl Resorcinol | | 0.20 | 0.20 |

Sun protection spray (all amounts in wt. %)

| Components | INCI | A | B | C |
|---|---|---|---|---|
| 4-Hexyl resorcinol | Hexylresorcinol | | 0.20 | 0.20 |
| 4-Butyl resorcinol | 4-Butylresorcinol | 0.20 | | 0.20 |

Sun protection spray O/W SPF 15-20

| Components | INCI | Amount |
|---|---|---|
| Dracorin ® GOC | Glyceryl oleate citrate. Caprylic/capric triglyceride | 2.00 |
| Corapan ® TQ | Diethylhexyl 2,6-naphthalate | 3.00 |
| Neo Heliopan ® HMS | Homosalate | 7.00 |
| Neo Heliopan ® OS | Ethylhexyl salicylate | 5.00 |
| Neo Heliopan ® 357 | Butyl methoxydibenzoyl methane | 3.00 |
| Isoadipate | Diisopropyl adipate | 6.00 |
| Baysilone ® Oil M10 | Dimethicone | 1.00 |
| Edeta ® BD | Disodium EDTA | 0.10 |
| Vitamin E acetate | Tocopheryl acetate | 0.50 |
| Dragosantol ® 100 | Bisabolol | 0.10 |
| Pemulen ® TR-2 | Acrylates/C10-30 alkyl acrylate crosspolymer | 0.25 |
| Glycerol 99.5 P | Glycerol | 4.00 |
| Butylene glycol | Butylene glycol | 5.00 |
| Neo Heliopan ® hydro (103089). Used as 25% aq. solution neutralized with Biotive ® L-Arginine | Phenylbenzimidazole sulfonic acid | 8.00 |
| Biotive ® L-Arginine | Arginine | 0.55 |
| SymWhite 377 | Phenylethyl Resorcinol | 0.1 |
| Perfume oil | Fragrance | 0.40 |
| Sobrol M | Methylparaben | 0.30 |
| SymWhite ® 377 | Phenylethyl Resorcinol | 0.20 |
| Water | Water (Aqua) | Ad 100 |

Sun protection soft cream W/O SPF 40

| Components | INCI | Amount |
|---|---|---|
| Dehymuls PGPH | Polyglyceryl-2 dipolyhydroxystearate | 5.00 |
| Copherol 1250 | Tocopheryl acetate | 0.50 |
| Permulgin 3220 | Ozocerite | 0.50 |
| Zinc stearate | Zinc stearate | 0.50 |
| Tegosoft TN | C12-15 alkyl benzoate | 10.00 |
| Neo Heliopan ® E1000 | Isoamyl-p-methoxycinnamate | 2.00 |
| Neo Heliopan ® 303 | Octocrylene | 5.00 |
| Neo Heliopan ® MBC | 4-methylbenzylidene camphor | 3.00 |
| Zinc oxide, neutral | Zinc oxide | 5.00 |
| EDETA BD | Disodium EDTA | 0.10 |
| Glycerol | Glycerol | 4.00 |
| Magnesium sulfate | Magnesium sulfate | 0.50 |
| Perfume oil P1, P2, P3, or P4 | Perfume | 0.30 |
| Symdiol ® 68 | 1,2-hexane diol. Caprylyl glycol | 0.30 |
| Dragosine | Carnosine | 0.10 |
| SymWhite ® 377 | Phenylethyl Resorcinol | 0.10 |
| Water, distilled | Water (aqua) | Add 100 |

Sun protection lotion W/O (all amounts in wt. %)

| Components | INCI | A | B | C |
|---|---|---|---|---|
| Dehymuls PGPH | Polyglyceryl-2 dipolyhydroxystearate | 3.00 | 3.00 | 3.00 |
| Beeswax 8100 | Beeswax | 1.00 | 1.00 | 1.00 |
| Monomuls 90-0-18 | Glyceryl oleate | 1.00 | 1.00 | 1.00 |
| Zinc stearate | Zinc stearate | 1.00 | 1.00 | 1.00 |
| Cetiol SN | Cetearyl isononanoate | 5.00 | 5.00 | 5.00 |
| Cetiol OE | Dicaprylyl ether | 5.00 | 5.00 | 5.00 |
| Tegosoft TN | C12-15 alkyl benzoate | 4.00 | 4.00 | 4.00 |
| Vitamin E | Tocopherol | 0.50 | 0.50 | 0.50 |
| Neo Heliopan ® OS | Ethylhexyl salicylate | 5.00 | 5.00 | 5.00 |
| Neo Heliopan ® AV | Ethylhexyl methoxycinnamate | 7.50 | 7.50 | 7.50 |
| Uvinul ® T150 | Ethylhexyl triazone | 1.50 | 1.50 | 1.50 |
| Trilon BD | Disodium EDTA | 0.10 | 0.10 | 0.10 |
| Glycerol | Glycerol | 5.00 | 5.00 | 5.00 |
| Neo Heliopan ® AP 10% solution. Neutralized with NaOH | Disodium phenyl dibenzimidazole tetrasulfonate | 15.00 | 15.00 | 15.00 |
| Perfume oil | Perfume | 0.25 | 0.25 | 0.25 |
| Alpha bisabolol | Bisabolol | 0.10 | 0.10 | 0.10 |
| SymOcide ® PT | Phenoxyethanol. Tropolone | 0.25 | 0.25 | 0.25 |
| SymWhite ® 377 | Phenylethyl Resorcinol | 0.5 | | |
| 4-Hexyl resorcinol | Hexylresorcinol | | 0.50 | |
| 4-Butyl resorcinol | 4-Butylresorcinol | | | 1.00 |
| Water, distilled | Water (Aqua) | ad 100 | ad 100 | ad 100 |

After-sun gel

| Components | INCI | Amount |
|---|---|---|
| SymSol ® PF-3 | Water (aqua). Pentylene glycol. Sodium lauryl sulfoacetate. Sodium oleoyl sarcosinate. Sodium chloride. Disodium sulfoacetate. Sodium oleate. Sodium sulfate | 3.00 |
| Glycerol 99.5 P. | Glycerol | 5.00 |
| SymUrban ® | Benzylidene dimethoxy dimethylene danone | 0.10 |
| Pemulen ® TR-2 | Acrylates/C10-30 alkyl acrylate crosspolymer | 1.00 |
| D-Panthenol 75 W | Panthenol | 0.50 |
| SymFinity ® 1298 | Echinacea purpurea extract | 0.10 |
| Extrapone ® Pearl GW | Water (aqua). Glycerol. Hydrolyzed pearl. Xanthan gum | 1.00 |
| Sodium hydroxide 10% solution | Sodium hydroxide | 2.50 |
| Ethanol 96% | Alcohol denat. | 15.00 |
| Perfume oil | Perfume | 0.20 |
| SymOcide ® PS | Phenoxyethanol. 1,2-Hexanediol. Decylene glycol | 0.50 |
| SymWhite ® 377 | Phenylethyl Resorcinol | 0.10 |
| Water | Water (aqua) | Ad 100 |

Night Recovery Cream

| Component | INCI | Amount |
|---|---|---|
| Aqua/Water | Aqua | ad 100 |
| SymSave ® H | Hydroxyacetophenone | 0.5 |
| SymDiol ® 68 | 1,2-Hexanediol Caprylyl Glycol | 0.5 |
| SymVital ® AR 3040 | Zingiber Officinale (Ginger) Root Extract | 0.2 |

Night Recovery Cream

| Component | INCI | Amount |
|---|---|---|
| Edeta ® BD | Disodium Edta | 0.1 |
| Emulsiphos ® | Potassium Cetyl Phosphate Hydrogenated Palm Glycerides | 2.0 |
| Mango Butter | *Mangifera Indica* Seed Butter | 2.0 |
| SymMollient ® S | Cetearyl Nonanoate | 1.0 |
| SymWhite ® 377 | Phenylethyl Resorcinol | 0.3 |
| Dragoxat ® 89 | Ethylhexyl Isononanoate | 8.5 |
| Lanette ® 16 | Cetyl Alcohol | 2.0 |
| Lanette ® O | Cetearyl Alcohol | 4.0 |
| SymRepair ® 100 | Hexyldecanol Bisabolol Cetylhydroxyproline Palmitamide Stearic Acid *Brassica Campestris* (Rapeseed) Sterols | 2.0 |
| Cetiol ® Ultimate | Tridecane Undecane | 5.0 |
| Carbopol ® Ultrez 10 Polymer | Carbomer | 0.3 |
| Tapioca Pure | Tapioca Starch | 2.0 |
| Fragrance | Parfum | 0.4 |
| Sodium Hydroxide 10% solution | Aqua Sodium Hydroxide | 0.4 |
| Tocopherol alpha DL | Tocopherol | 0.5 |

Fresh watering after sun mousse

| Component | INCI | Amount |
|---|---|---|
| Aqua/Water | Aqua | Ad 100 |
| SymSol ® PF-3 | Aqua Pentylene Glycol Sodium Lauryl Sulfoacetate Sodium Oleoyl Sarcosinate Sodium Chloride Sodium Oleate | 2.0 |
| Aqua Keep 10SH-NFC | Sodium Acrylates Crosspolymer-2 | 2.0 |
| SymSave ® H | Hydroxyacetophenone | 0.5 |
| SymDiol ® 68 | 1,2-Hexanediol Caprylyl Glycol | 0.5 |
| Hydrolite ® 5 | Pentylene Glycol | 3.0 |
| SymWhite ® 377 | Phenylethyl Resorcinol | 0.2 |
| SymGlucan ® | Aqua Glycerin 1,2-Hexanediol Caprylyl Glycol Beta-Glucan | 1.0 |
| Lanette ® O | Cetearyl Alcohol | 1.0 |
| SymRepair ® 100 | Hexyldecanol Bisabolol Cetylhydroxyproline Palmitamide Stearic Acid *Brassica Campestris* (Rapeseed) Sterols | 1.0 |
| SymSitive ® 1609 | Pentylene Glycol 4-T-Butylcyclohexanol | 1.0 |
| Frescolat ® Ml | Menthyl Lactate | 1.0 |
| SymMollient ® S | Cetearyl Nonanoate | 2.5 |
| Dragoxat ® 89 | Ethylhexyl Isononanoate | 5.0 |
| Isodragol ® | Triisononanoin | 3.0 |
| SymUrban ™ | Benzylidene Dimethoxydimethylindanone | 0.3 |
| Xiameter ® | Dimethicone Dimethiconol | 1.0 |
| Fragrance | Parfum | 0.3 |

Creme gel for face

| Component | INCI | Amount |
|---|---|---|
| Aqua/Water | Aqua | ad 100 |
| SymWhite ® 377 | Phenylethyl Resorcinol | 0.15 |
| Sclareolide | Sclareolide | 0.10 |
| Glycerin | Glycerin | 3.0 |
| Dracorin ® Goc | Glyceryl Oleate Citrate Caprylic/Capric Triglyceride | 0.3 |
| Jojoba Oil | *Simmondsia Chinensis* Seed Oil | 4.0 |
| Avocado Oil | *Persea Gratissima* Oil | 4.0 |
| Sweet Almond Oil | *Prunus Amygdalus Dulcis* (Sweet Almond) Oil | 4.0 |
| Shea Butter | *Butyrospermum Parkii* Butter | 2.0 |
| Symdecanox Ha | Caprylic/Capric Triglyceride Hydroxymethoxyphenyl Decanone | 1.0 |
| SymWhite ® 377 | Phenylethyl Resorcinol | 0.2 |
| Cosmedia Sp | | 1.2 |
| Symocide ® Ps | Phenoxyethanol Decylene Glycol 1,2-Hexanediol | 1.0 |
| Tapioca Pure | Tapioca Starch | 1.0 |

Creamy fresh body lotion

| Component | INCI | Amount |
|---|---|---|
| Emulsiphos ® | Potassium Cetyl Phosphate Hydrogenated Palm Glycerides | 2.50 |
| Tegin M | Glyceryl Stearate | 1.20 |
| Pcl-Solid ® | Stearyl Heptanoate Stearyl Caprylate | 2.00 |
| Silcare ® Silicone 41m15 | Caprylyl Methicone | 4.00 |
| Tocopheryl Acetate | Tocopheryl Acetate | 0.25 |
| Lanette ® 16 | Cetyl Alcohol | 0.50 |
| PCL-Liquid ® 100 | Cetearyl Ethylhexanoate | 5.00 |
| Xiameter ® Pmx-200 Silicone Fluid 100cs | Dimethicone | 2.00 |
| Symvital ® AR 3040 | *Zingiber Officinale* (Ginger) Root Extract | 0.10 |
| SymWhite ® 377 | Phenylethyl Resorcinol | 0.20 |
| Tego ® Feel Green | Cellulose | 1.00 |
| Keltrol ® Cg-F | Xanthan Gum | 0.30 |
| Extrapone ® Watermint P | Aqua Propylene Glycol Glucose *Mentha Aquatica* Leaf Extract | 1.00 |
| Glycerin | Glycerin | 4.00 |
| Extrapone ® Deep Sea Gw | Aqua Glycerin *Thermus Thermophillus* Ferment | 1.00 |
| Symwhite Plus ® | Caprylic/Capric Triglycerides, Pentylene Glycol, Phenylethyl Resorcinol, Bisabolol, Butyl Methoxydibenzoyl Methane | 2.00 |
| Hydrolite ® 5 | Pentylene Glycol | 4.00 |
| Symsave ® H | Hydroxyacetophenone | 0.50 |
| Colour | | 0.81 |
| Dragosine ® | Carnosine | 0.10 |
| Frescolat ® ML | Menthyl Lactate | 0.50 |
| Fragrance | Parfum | 0.50 |
| Aqua/Water | Aqua | Ad 100 |

Eye lotion

| Component | INCI | Amount | Amount |
|---|---|---|---|
| Dracorin ® GOC | Glyceryl Oleate Citrate Caprylic/Capric Triglyceride | 2.50 | 2.50 |
| Pcl-Liquid ® 100 | Cetearyl Ethylhexanoate | 2.50 | 2.50 |
| Isodragol ® | Triisononanoin | 4.00 | 4.00 |

-continued

| Eye lotion | | | |
|---|---|---|---|
| Component | INCI | Amount | Amount |
| Symmollient ® S | Cetearyl Nonanoate | 1.50 | 1.50 |
| Xiameter ® Pmx-200 Silicone Fluid 350 Cs | Dimethicone | 1.00 | 1.00 |
| Dragosine ® | Carnosine | 0.10 | 0.10 |
| Tocopheryl Acetate | Tocopheryl Acetate | 0.10 | 0.10 |
| Carbopol ® Etd 2020 Polymer | Acrylates/C10-30 Alkyl Acrylate Crosspolymer | 0.15 | 0.15 |
| Keltrol ® Cg-T | Xanthan Gum | 0.25 | 0.25 |
| Symsave ® H | Hydroxyacetophenone | 0.50 | 0.50 |
| Symdiol ® 68 | 1,2-Hexanediol CAPRYLYL GLYCOL | 0.50 | 0.50 |
| Sodium Hydroxide 10% Sol. | Aqua, Sodium Hydroxide | 0.20 | 0.20 |
| Simulgel Ns | Hydroxyethyl Acrylate/Sodium Acryloyldimethyl Taurate Copolymer SQUALANE POLYSORBATE 60 | 0.60 | 0.60 |
| Hydroviton ® Plus | Aqua, Pentylene Glycol, Glycerin, Fructose, Urea, Citric Acid, Sodium Hydroxide, Maltose, Sodium Pca, Sodium Chloride, Sodium Lactate, Trehalose, Allantoin, Sodium Hyaluronate, Glucose | 2.00 | 2.00 |
| SymWhite ® 377 | Phenylethyl Resorcinol | 0.15 | 0.10 |
| Larixol | Larixol | — | 0.10 |
| Symfinity ® 1298 | Echinacea Purpurea Extract | 0.10 | 0.10 |
| Fragrance | Parfum | 0.30 | 0.30 |
| Aqua/Water | Aqua | ad 100 | ad 100 |

The invention claimed is:

1. A cosmetic method for treating hyperpigmentation in a subject in need thereof, comprising the following steps:
   (i) providing a cosmetic composition consisting of
   (1-a) at least one resorcinol derivative of formula (I)

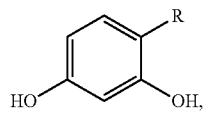

in which R is an alkyl radical having 3 to 10 carbon atoms or a substituted alkylphenyl radical having 8 to 16 carbon atoms,
   (1-b) a carrier,
   (i-c) ginger root $CO_2$ extract, and
   (ii) applying said cosmetic composition of step (i) to skin wherein said cosmetic composition is a cream, lotion, gel, paste or capsule.

2. The method of claim 1, wherein said resorcinol derivative is phenylethyl resorcinol.

3. The method of claim 1, wherein said composition comprises the resorcinol derivative of formula (I) in an amount from 0.01 wt.-percent to 10 wt.-percent, based on the total amount of the cosmetic composition.

4. The method of claim 1, wherein said ginger root $CO_2$ extract consists of:
   (a) 15 to 30% b.w. [6]-gingerol
   (b) 3 to 10% b.w. [8]-gingerol
   (c) 3 to 10% b.w. [10]-gingerol
   (d) 0.5 to 4% b.w. [6]-shogaol
   (e) 0.03 to 1.3% b.w. [8]-shogaol;
   (f) 0.03 to 1% b.w. [10]-shogaol;
   (g) 0.01 to 1% b.w. zingerone,
on condition that the amount of gingerols sums up to 24 to 50% b.w. and the amount of shogaols sums up to 0.5 t 6% b.w.

5. The method of claim 1, wherein said ginger root $CO_2$ extract consists of:
   (a) 25 to 30% b.w. [6]-gingerol
   (b) 5 to 10% b.w. [8]-gingerol
   (c) 5 to 10% b.w. [10]-gingerol
   (d) 1.5 to 4% b.w. [6]-shogaol
   (e) 0.3 to 1.3% b.w. [8]-shogaol;
   (f) 0.03 to 1% b.w. [10]-shogaol;
   (g) 0.01 to 1% b.w. zingerone,
on condition that the amount of gingerols sums up to 35 to 50% b.w. and the amount of shogaols sums up to 1.5 t 6% b.w.

6. The method of claim 1, wherein said ginger root $CO_2$ extract consists of:
   (a) 15 to 25% b.w. [6]-gingerol
   (b) 3 to 5% b.w. [8]-gingerol
   (c) 3 to 8% b.w. [10]-gingerol
   (d) 0.5 to 3% b.w. [6]-shogaol
   (e) 0.03 to 1% b.w. [8]-shogaol;
   (f) 0.03 to 1% b.w. [10]-shogaol;
   (g) 0.01 to 1% b.w. zingerone,
on condition that the amount of gingerols sums up to 24 to 35% b.w. and the amount of shogaols sums up to 0.5 to 5% b.w.

7. The method of claim 1, wherein the hyperpigmentation is induced by the radiation of light within a wave-length from 400 to 750 nm.

8. A cosmetic method for treating hyperpigmentation in a subject in need thereof, comprising the following steps:
   (i) providing a cosmetic composition consisting of
      (1-a) at least one resorcinol derivative of formula (I)

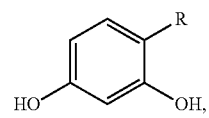

in which R is an alkyl radical having 3 to 10 carbon atoms or a substituted alkylphenyl radical having 8 to 16 carbon atoms,
   (1-b) a carrier,
   (1-c) ginger root $CO_2$ extract, and
   (1-d) carnosine, and
   (ii) applying said cosmetic composition of step (i) to skin.

9. The method of claim 8, wherein the hyperpigmentation is induced by the radiation of light within a wave-length from 400 to 750 nm.

* * * * *